(12) United States Patent
Arii et al.

(10) Patent No.: US 7,989,761 B2
(45) Date of Patent: Aug. 2, 2011

(54) GAS ANALYZING METHOD AND GAS ANALYZING APPARATUS

(75) Inventors: Tadashi Arii, Fussa (JP); Kyoji Matsumoto, Koganei (JP); Satoshi Otake, Tachikawa (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 311 days.

(21) Appl. No.: 12/347,377

(22) Filed: Dec. 31, 2008

(65) Prior Publication Data

US 2009/0173879 A1 Jul. 9, 2009

(30) Foreign Application Priority Data

Jan. 8, 2008 (JP) ................................. 2008-001651

(51) Int. Cl.
*H01J 49/00* (2006.01)
*H01J 49/14* (2006.01)
*B01D 59/44* (2006.01)

(52) U.S. Cl. ......... 250/288; 250/281; 250/282; 250/290
(58) Field of Classification Search .................. 250/288, 250/281, 282, 290
See application file for complete search history.

(56) References Cited

U.S. PATENT DOCUMENTS

| 7,227,134 B2* | 6/2007 | Miller et al. | 250/288 |
| 7,381,944 B2* | 6/2008 | Cameron et al. | 250/282 |
| 7,714,284 B2* | 5/2010 | Miller et al. | 250/295 |
| 2007/0181801 A1 | 8/2007 | Yamada et al. | |
| 2009/0026362 A1* | 1/2009 | Arii et al. | 250/281 |

FOREIGN PATENT DOCUMENTS

| EP | 2006672 A1 | 12/2008 |
| WO | WO 2007/108211 A1 | 9/2007 |

OTHER PUBLICATIONS

Search Report issued in corresponding German Patent Application No. 10 2009 004 398.5 Dated: Jan. 8, 2009.

* cited by examiner

*Primary Examiner* — Nikita Wells
(74) *Attorney, Agent, or Firm* — Buchanan Ingersoll & Rooney PC

(57) ABSTRACT

Ions obtained through EI process from a first gas are subjected to mass analysis to obtain ion intensities which are stored in a first file, and ions obtained through soft ionization process from a second gas having same concentration of components as that of the first gas are subjected to mass analysis to obtain ion intensities which stored in a second file, and molecular weights are determined based on parent ions from soft ionization measurement data. A mass spectrum corresponding to the determined molecular weight is read out based on an NIST database, and the ion intensity data stored in the first file and the read out NIST data are compared with each other, and component molecules of the first gas are determined based on the comparison results. Qualitative analysis of mixed gas can be conducted in real time with high accuracy by making effective use of the measurement data of both mass analysis based on EI process and mass analysis based on soft ionization process.

17 Claims, 15 Drawing Sheets

| m/z | NAMES OF COMPOUNDS | EI SPECTRUM |
|---|---|---|
| 78 | ARSINE |  |
| 78 | BENZENE |  |
| ⋮ | ⋮ | ⋮ |
| 92 | TOLUENE |  |
| ⋮ | ⋮ | ⋮ |
| 106 | XYLENE |  |
| ⋮ | ⋮ | ⋮ |
|  |  |  |

FIG.5

| m/z | IONIZATION EFFICIENCY |
|---|---|
| 78 | ○○○○ |
| ⋮ | ⋮ |
| 92 | ○○○○ |
| ⋮ | ⋮ |
| 106 | ○○○○ |
| ⋮ | ⋮ |
|  |  |

(EI MASS SPECTRUM) IN DATABASE (EI MASS SPECTRUM) IN DATABASE (EI MASS SPECTRUM) IN DATABASE

COMBINED MASS SPECTRUM

GAS ANALYZING METHOD AND GAS ANALYZING APPARATUS

BACKGROUND OF THE INVENTION

1. Field of the Invention

The present invention relates to a gas analyzing method and a gas analyzing apparatus that perform qualitative analysis as a technique to determine component gas contained in mixed gas.

2. Description of the Related Art

There has been known a technique for qualitative analysis, which utilizes mass analysis process based on Electro-Impact Ionization (hereinafter referred to as EI) and a library searching system. This method ionizes a sample gas through EI process, separates ions for each mass-to-charge ratio (m/z) to measure ion intensities thereof, and thus obtains mass spectrum. The mass spectrum is a graph with abscissa axis being m/z (mass-to-charge ratio) and ordinate axis being ion intensity. Hereinafter, measurement data of mass spectrums obtained based on EI may be referred to as EI measurement data.

The obtained mass spectrum is identified by using a library searching system which includes a database for reference (also referred to as a reference database), such as NIST (National Institute of Standards and Technology), that is, a material name is determined based on the obtained mass spectrum. Specifically, each of a plurality of mass spectrum data stored within the reference database and EI measurement data are compared with each other through a profile fitting, to thereby determine its material name.

The EI process uses relatively high energy, such as 70 eV, for ionizing gas. Therefore, the EI process does not choose specific kinds of gas to be ionized, that is, it is applicable to nearly all kinds of volatile compounds. In the EI process, when high energy of 70 eV is supplied to component molecules of gas, fragment ions generated due to fragmentation of the parent molecules contained in gas are observed as well as ions (i.e., parent ions) generated correspondingly to parent molecules. The fragment ions yield an important factor in estimating the structure of molecules which is forming the gas. However, a plurality of mass spectrums stored in the reference database corresponds to gases having single component, respectively. In the case that the gas being the target of qualitative analysis is a mixed gas composed of a plurality of component molecules, there is a problem that, when using the library searching system, the generation of the fragment ion results in acting as interfering ion on the contrary and thus makes it difficult to identify components, and eventually a highly accurate qualitative analysis cannot be made.

In order to realize analysis of such a mixed gas, there has been conventionally proposed a qualitative analysis through, for example, a gas chromatography mass analysis method (GC/MS), as illustrated in FIG. 14. In the method, the mixed gas is collected by a trap and then decomposed into a plurality of, for example, three: A, B and C component gases by means of a gas chromatograph (GC) on time-series basis. Subsequently, component gases are introduced into a mass analysis device (MS) sequentially. The reason for collecting gases by the trap is that the next gas sample cannot be introduced within the period of time (a few minutes to ten and a few minutes) during which the separation by the GC is performed.

In the mass analysis device (MS), respective steps of the EI process, ion separation, and ion intensity measurement are executed, and then mass spectrums of decomposed component gases A, B and C are measured, respectively. An operation processing device provided at a latter part of the mass analysis device (MS), for example, is configured to include a computer, and performs control as illustrated in FIG. 15. That is, the operation processing device stores EI measurement data (i.e., mass spectrums) of respective gas components A, B and C in a memory and may select one from among them. Then, the operation processing device makes comparison between selected EI measurement data and reference data (i.e., mass spectrums) read out from the NIST database in terms of m/z (mass-to-charge ratio) and ion intensity, determines substance names for the EI measurement data, and stores them in the memory. The device performs the processing for other component gases B, C too, and finally identifies component gases contained in the mixed gas from the substance names stored within the memory.

According to the aforementioned GC/MS, since a fragment ions derived from one parent ion never overlaps fragment ion derived from another parent ion, the GC/MS is capable of correctly identifying component gases. However, if a mixed gas is, for example, an unknown component sample evolved from a sample, there is a problem that evolved gas cannot be analyzed in real time, because gases must be collected by means of the trap. In the GC/MS, there may also be another obstacle for analysis due to heat instability or the like of unstable component gases including radicals.

It is to be noted that, "real time analysis" means:
directly analyzing a gas evolving from gas source such as a sample, etc., the gas changing its components, ratio of components (i.e., concentration) or the like with the lapse of time;
analyzing it simultaneously or instantaneously;
analyzing it without once collecting it;
analyzing it without adding secondary process; or
analyzing it in a state maintaining component content and ratio of components when it has been evolved.

There have been known ionizations, such as chemical ionization, photo-ionization, etc., that can suppress occurrence of fragment ions, which may be a disadvantage of EI. These ionizations are sometimes called soft ionization since they can suppress occurrence of fragment ions. According to the soft ionization, since only component molecules of gas can be selectively ionized and observed, each gas component contained in a mixed gas can be identified in real time for each molecule ion. However, in a mass analysis based on the soft ionization, what can be obtained is only molecule ion information, so that there is a problem that components having the same mass ions cannot be discriminated from each other. Further, results of the mass analysis based on the soft ionization do not have structure information given by fragment ions, so that there is also a problem that accurate qualitative analysis cannot be always made.

The present inventors have already proposed a mass analysis device that has both functions of EI process and soft ionization process. Such a mass analysis device is disclosed in, for example, PCT Publication WO2007/108211 pamphlet (page 20-48, FIG. 1). The PCT Publication WO2007/108211 describes in greater detail a technique of how to independently carry out each of the EI process and soft ionization process, and how to carry out them simultaneously. In addition, it briefly teaches advantage of obtaining the both of EI measurement data and soft ionization measurement data. However, it does not teach the use of the EI measurement data and the soft ionization measurement data for qualitative analysis of mixed gas and other gas analyzing techniques.

As described above, in a method based on the EI process and the library searching, there is a problem that qualitative analysis cannot be conducted with sufficient accuracy due to overlap of fragment ions, in the case that the analysis target is a mixed gas. Additionally, in the measurements based on the soft ionization process such as PI process, since identification of component molecules cannot be made in a region where ion peaks overlap, all the same, qualitative analysis of mixed gas cannot be conducted with sufficient accuracy. Also, in the qualitative analysis of mixed gas through GC/MS, although accuracy of the qualitative analysis is enhanced, there is a problem that real time analysis cannot be conducted.

SUMMARY OF INVENTION

The present inventors have been making earnest efforts aiming at the increase in analysis accuracy when conducting qualitative analysis of mixed gas in real time. As a result, they came to believe that, if results of the analysis that has employed the soft ionization process are utilized in addition to an analysis that has employed the EI process, it will in turn lead to increase in analysis accuracy while maintaining real time analysis.

Accordingly, the present invention is directed to provide a gas analyzing method and a gas analyzing apparatus that enable qualitative analysis of mixed gas in real time with high accuracy by making effective use of measurement data of the both of mass analysis based on the EI process and mass analysis based on the soft ionization process.

A gas analyzing method according to the present invention is a gas analyzing method for determining components of a first gas, comprising: a first mass analysis step of measuring an intensity of ion obtained from the first gas through an electro impact ionization process; a second mass analysis step of measuring an intensity of ion obtained through soft ionization process from a second gas having same concentration of components as those of the first gas; a molecular weight determination step of determining molecular weights based on parent ion from data obtained in the second mass analysis step; a reference data read-out step of reading out mass spectrums corresponding to molecular components determined in the molecular weight determination step, based on a reference database generated by storing mass spectrums of compounds for each compound in case of exciting the compounds through electro impact ionization method; and a comparison step of comparing ion intensity data obtained in the first mass analysis step with data read out in the reference data read-out step, wherein components of the first gas are determined based on the comparison result in the comparison step.

In the above-described configuration, the first gas is a gas that is going to be subjected to qualitative analysis, and the second gas is a gas for reference that is used to enhance accuracy of the qualitative analysis. The first gas and second gas may be gases that evolved from a sample at different moments of time, may be gases that evolved alternately from a sample at different moments of time within a predetermined period of time, may be gases that evolved from separate samples obtained by dividing a sample, or may be gases that evolved from separate samples having the same molecular structures.

According to a gas analyzing method of the present invention, component molecules of a first gas and those of a second gas are the same, and thus we decide to take the process as follows: obtaining measurement data of EI (electro impact ionization) through a first mass analysis step; obtaining measurement data of soft ionization through a second mass analysis step; estimating molecular weights of component molecules of the second gas from measurement data of soft ionization; narrowing down reference data (NIST data, etc.) based on the molecular weights to eliminate unnecessary data; and then comparing the reference data with EI measurement data to identify substance names of component molecule of the first gas, that is, to conduct qualitative analysis of the first gas. For this reason, avoided is the necessity to make comparison for all of a huge volume of data such as the NIST data, and accordingly, accurate qualitative analysis can be conducted in a short period of time. Moreover, memory capacity and computation processing time can be greatly reduced when performing comparing process.

In a gas analyzing method according to the present invention, (1) molecular weights of a plurality of parent ions may be determined through a molecular weight determination step; (2) mass spectrums corresponding to each of molecular weights of a plurality of parent ions maybe read out through a reference data read-out step, (3) in a comparison step, these multiple mass spectrums may be combined to obtain combined mass spectrums, and ion intensity data obtained in the first mass analysis step may be compared with the combined mass spectrums.

Also, in a gas analyzing method according to the present invention, (1) molecular weights of multiple parent ions may be determined through a molecular weight determination step, (2) mass spectrums corresponding to each of molecular weights of multiple parent ions may be read out through a reference data read-out step, (3) in the comparison step, readout mass spectrums may be compared with ion intensity data obtained in the first mass analysis step on one-by-one basis. Then, in this case, multiple mass spectrums may be compared in increasing order of molecular weights, and further, it is desirable to subtract mass spectrums corresponding to the relevant molecular weights after individual comparisons from ion intensity data before comparisons.

A search algorithm of mass spectrums generally performs profile fitting using signals with high ion intensity and signals with large molecular weights. As a result, in the case that analysis target is mixed gases, it becomes hard to distinguish component with small molecular weights from fragments of large molecule, and it is hard to make qualitative analysis. Since information on low mass components can be found in soft ionization, it is surely possible to target low mass components, which used to be hardly caught by searching, for search by utilizing this information so as to start searching from low mass components earlier than others.

In a gas analyzing method according to the present invention, it is desirable to determine intensity ratio among multiple parent ions from data based on soft ionization, and multiply mass spectrums read out from the reference database by their ion intensity ratios. An ion intensity ratio means a concentration ratio of each component molecule to the entire mixed gases. Since the data of library spectrums (e.g., reference database) is standardized in terms of their ion intensity, actual intensity factors are not included in comparing process and subtracting process. The qualitative probability can be enhanced by acquiring information on the quantity of evolved gases from soft ionization measurement data, and adding the information to search algorithm.

In a gas analyzing method according to the present invention, it is desirable to read out ionization efficiencies of compounds corresponding to molecule components determined based on measurement data of soft ionization from ionization efficiency database made by storing the ionization efficiencies for each molecular weight of compounds, to multiply mass spectrums for each molecular component read out from the reference database by ionization efficiencies corresponding to the relevant molecular weights. Then, it is desirable to compare reference data after the multiplying process with EI measurement data.

Now, a gas analyzing apparatus according to the present invention is a gas analyzing apparatus for determining components of a first gas, comprising: (1) a first mass analysis means that ionizes the first gas through electro impact ionization process, separates the ion for each m/z, and measures intensity of the ion for each m/z; (2) a second mass analysis means that ionizes a second gas having same concentration of components as those of the first gas through soft ionization process, separates the ion for each m/z, and measures intensity of the ion for each m/z; (3) a molecular weight determination means that determines molecular weight based on parent ion from data obtained by the second mass analysis means; (4) a reference data read-out means that reads out mass spectrums corresponding to molecular weights determined by the molecular weight determination means, based on a reference database made by storing mass spectrums of compounds of single component for each molecular weight of compounds in case of exciting the compounds through electro impact ionization process; and (5) a determination means that compares ion intensity data obtained by the first mass analysis means with data read out by the reference data read-out means, and thereby determines components of the first gas.

In the above-described configuration, a molecular weight determination means, reference data read-out means, and determination means may be achieved through functions that can be realized by means of a program stored within CPU and memory of computer, for example.

According to a gas analyzing apparatus of the present invention, component molecules of a first gas and component molecules of a second gas are the same. EI measurement data are obtained by means of a first mass analyzing means, and measurement data of soft ionization is obtained by means of a second mass analyzing means. Then, molecular weights of component molecules of the second gas are estimated from the measurement data of the soft ionization by means of molecular weight determination means. Then, reference data (NIST data, etc.) is narrowed down by means of reference data read-out means based on the estimated molecular weights, and unnecessary data is eliminated. Then, the reference data and EI measurement data are compared by means of determination means, and identification of substance names of component molecules of a first gas, that is, qualitative analysis of a first gas is carried out. As the results of combinations of the above structural elements, avoided is the necessity to target all of a huge volume of data such as NIST data for comparisons, and accordingly accurate qualitative analysis can be conducted in a short period of time. Moreover, when performing a comparing process, memory capacity and computation processing time can be significantly reduced.

In a gas analyzing apparatus according to the present invention, (1) a molecular weight determination means may determine molecular weights of multiple parent ions; (2) a reference data read-out means may read out mass spectrums corresponding to each of molecular weights of the multiple parent ions that have been determined; (3) the determination means may combine their multiple mass spectrums to obtain combined mass spectrums, and may compare ion intensity data measured by means of the first mass analyzing means with the combined mass spectrums.

In a gas analyzing apparatus according to the present invention, (1) a molecular weight determination means may determine molecular weights of multiple parent ions; (2) a reference data read-out means may read out mass spectrums corresponding to each of molecular weights of the multiple parent ions that have been determined; (3) the determination means may compare on one-by-one basis mass spectrums that have been read out, with ion intensity data that have been measured by means of the first mass analyzing means. Then, in this case, (4) it is desirable that the determination means compares read-out mass spectrums in increasing order of molecular weights, and subtracts mass spectrums corresponding to the relevant molecular weights after individual comparisons from ion intensity data before comparisons.

In a gas analyzing apparatus according to the present invention, it is desirable that the determination means obtains intensity ratios among the multiple parent ions measured by means of the first mass analyzing means, and multiplies mass spectrums read out from the reference database by ion intensity ratios.

Further, a gas analyzing apparatus according to the present invention can further have ionization efficiency database generated by storing ionization efficiencies of compounds for each molecular component of compounds, and it is desirable that the determination means reads out ionization efficiencies corresponding to the determined molecular components from the ionization efficiency database, and multiplies mass spectrum for each molecule component read out from the reference database by ionization efficiency corresponding to the relevant molecular component.

As described above, according to a gas analyzing method and gas analyzing apparatus of the present invention, EI measurement data obtained through measurements is not directly searched from massive volumes of NIST data, but compared with EI measurement data in a state where NIST data has been narrowed down in advance by making effective use of data of molecular weights obtained from PI measurement data and the number of evolved gases. For this reason, finally obtained determination results are very accurate, and thus the number of data that will be objects of computation can be substantially reduced, and moreover, memory capacity and computation processing time can be substantially reduced.

BRIEF DESCRIPTION OF THE DRAWINGS

FIG. 5 is a view illustrating an example of storage content of an ionization efficiency database.

DESCRIPTION OF THE PREFERRED EMBODIMENTS

First Embodiment of Gas Analyzing Method and Gas Analyzing Apparatus

Hereinafter, a gas analyzing method and a gas analyzing apparatus according to the present invention will be described based on an embodiment. It is to be noted that, as a matter of course, the present invention is not limited to the embodiment. Also, drawings will be referred to in the following description, but components may be represented in different ratios from actual ones in these drawings in order to illustrate characteristic parts in a form suitable for easy understanding.

Figure 1:
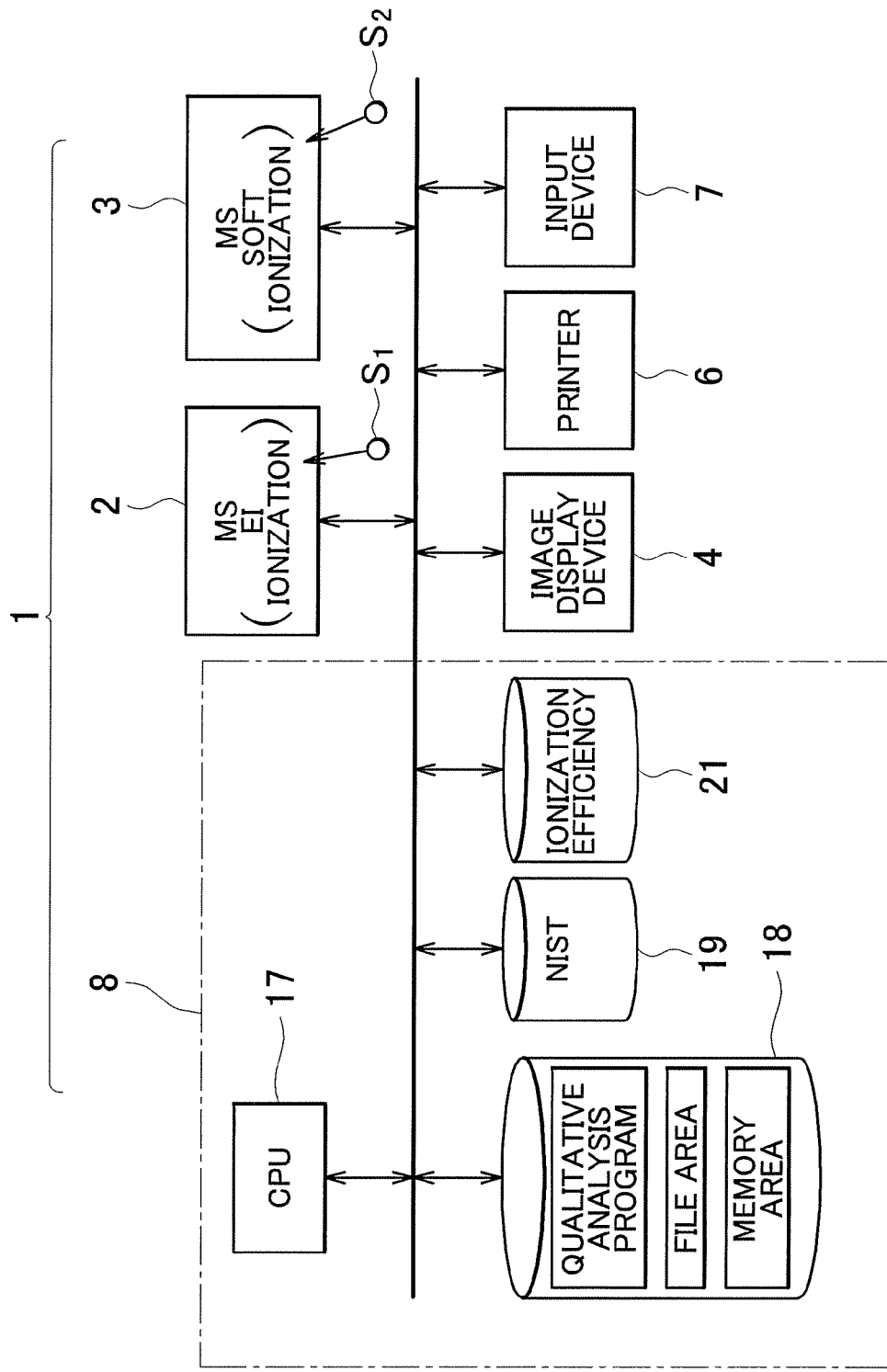
FIG. 1 is a block diagram illustrating an embodiment of a gas analyzing apparatus that implements a gas analyzing method according to the present invention.

FIG. 1 shows an embodiment of a gas analyzing apparatus for implementing a gas analyzing method according to the present invention. The gas analyzing apparatus 1 includes an EI mass analysis device 2, a soft mass analysis device 3, an image display device 4, a printer 6, an input device 7, and a control device 8. The image display device 4 is formed by a flat panel display, such as a liquid crystal display, for example. The printer 6 is formed by, for example, a printer using electrostatic transfer method. The input device 7 may be a mouse, a keyboard, and the like.

Figure 2A:
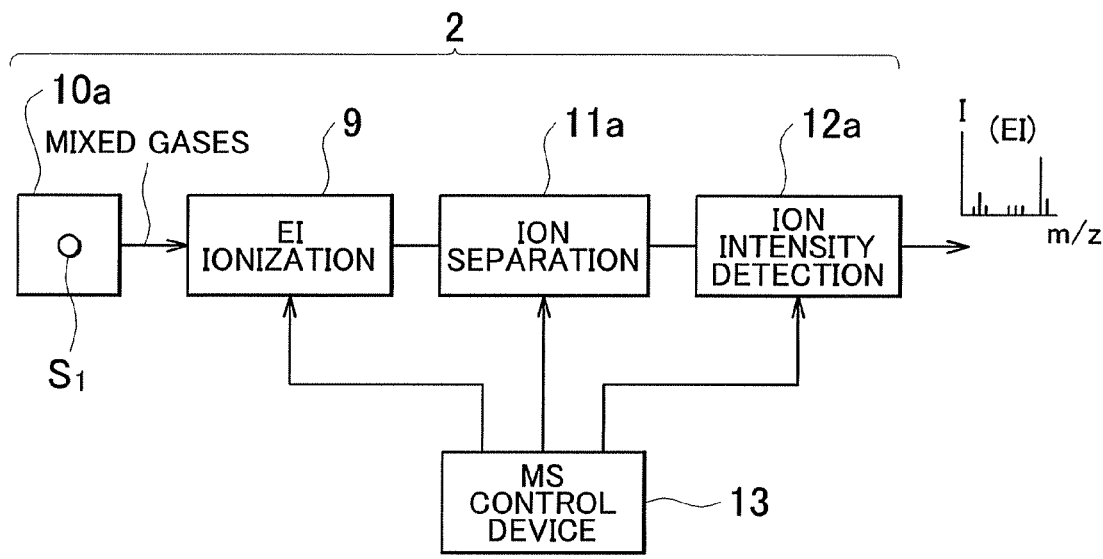
FIGS. 2A and 2B illustrate mass analysis devices being a main part of device of FIG. 1, FIG. 2A illustrating mass analysis device in accordance with EI method and FIG. 2B illustrating mass analysis device in accordance with soft ionization method, respectively.

The EI mass analysis device 2 includes, for example, as shown in FIG. 2A, a sample processing unit 10a, an electro impact ionization device (hereinafter may be referred to as EI device) 9, an ion separation device 11a, an ion intensity detection device 12a, and an MS control device 13 configured to control their operations. The sample processing unit 10a has any desired structure that allows a sample to be fixedly arranged, and further has a temperature regulator around the location where the sample is arranged. The temperature regulator has a heater and a cooler as needed, and causes the temperature of a sample S1 to rise and to decrease as needed in accordance with a predetermined program. In the present embodiment, gas evolved from the sample S1 is a target of gas analysis.

The EI device 9 is a device for ionizing molecules that form gas introduced therein. The EI device 9 uses a technique to generate ions, for example, by causing electrons to collide against molecules, thereby releasing electrons in the molecules. Electric current is passed through, for example, a filament, so that electrons to be hit against the molecules can be taken out from the filament as thermal electrons. An ion corresponding to a molecule may be called a parent ion. Molecules are cleaved when electrons are caused to collide against the molecules, such that fragment ions are generated together with parent ions within a wide range of m/z (mass-to-charge ratio). The parent ions provide information related to molecular weights of the molecules that make up a gas, and the fragment ions provide information on the structure of the molecules.

The ion separation device 1a is a device that separates generated ions for each mass-to-charge ratio (m/z) to supply them to the ion intensity detection device 12a, and separates ions for each mass by utilizing electric field or magnetic field, for example. A device that utilizes electric field may be a quadrupole ion separation device which has four rod-shaped electrodes aligned parallel with each other, and separates ions for each mass by controlling voltages applied thereto. The ion intensity detection device 12a is constructed using an electron multiplier that emits electrons when an ion is applied thereto. At an output terminal of the ion intensity detection device 12a, ion intensity (I) is output for each mass-to-charge ratio (m/z). A mass spectrum shows the relationship between them as a graph. The EI mass analysis device 2 provides mass spectrums as measurement results, which include peaks of parent ions and peaks of fragment ions.

Figure 2B:
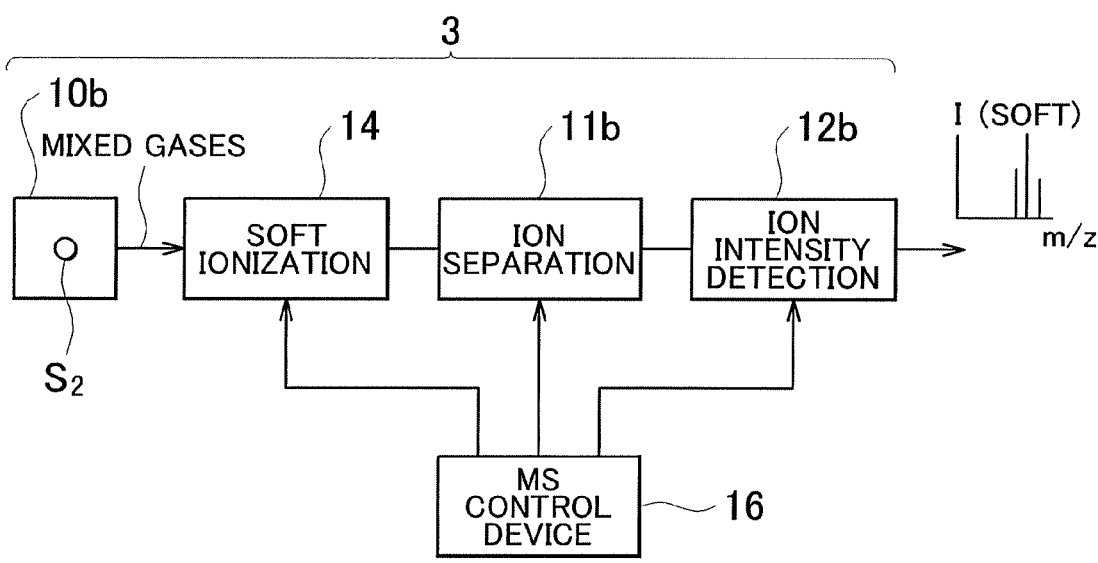

The soft mass analysis device 3 of FIG. 1 includes, for example, as illustrated in FIG. 2B, a sample processing unit 10b, a soft ionization device 14, an ion separation device 11b, an ion intensity detection device 12b, and an MS control device 16 that controls their operations. The ion separation device 11b and the ion intensity detection device 12b have the same configurations as those of the ion separation device 11a and the ion intensity detection device 12a as used in the EI mass analysis device 2, respectively.

The sample processing unit 10b has any desired structure in which samples can be arranged fixedly, in a similar manner to the sample processing unit 10a of the EI mass analysis device 2, and further has a temperature regulator around the location where the sample is arranged. The temperature regulator has a heater and a cooler as needed, and causes temperatures of sample S2 to rise and to decrease as needed in accordance with a predetermined program. In normal measurements, the sample S2 is made of the same substance as that of the sample S1. Also, temperature rising and decreasing program by the temperature regulator is rendered to exactly match the program at the sample processing unit 10a of the EI mass analysis device 2. That is, temperatures of the both samples are controlled such that, if any thermal change occurs in the sample S1, similar thermal change will occur without exception in the sample S2 too.

The soft ionization device 14 is a device that ionizes molecules composing a gas introduced therein. The device, in particular, ionizes only component molecules without developing the cleavage of ions. The ion intensity detection device 12b of the soft mass analysis device 3 also output, at an output terminal thereof, ion intensity (I) for each mass-to-charge ratio (m/z). The soft mass analysis device 3 gives mass spectrums as measurement results, which includes only peaks of parent ions without including fragment ions.

The soft ionization device 14 is constructed using, for example, a photo-ionization device, a chemical ionization device or the like. The photo-ionization device and the chemical ionization device may be called PI device and CI device, respectively. The PI device is a device for irradiating a molecule with light to ionize the molecule. The light may be ultraviolet light, vacuum ultraviolet light, soft X-ray, etc., which are mentioned in the decreasing order of wavelength. Laser beam can be also used. The CI device causes a reaction gas molecule that has been ionized, to collide against component molecules of a gas, so as to ionize the component molecules. The reaction gas may be called a reagent gas. The ionization of a reaction gas molecule is performed on EI principle. PI process as well as CI process can provide only ions related to molecular weights without developing cleavage when ionizing molecules.

In FIG. 1, the EI mass analysis device 2 and the soft mass analysis device 3 are installed as separate devices. Then, a sample S1 to be measured is mounted at a predetermined position within the sample processing unit 10a of the EI mass analysis device 2 (see FIG. 2A). Also, a reference sample S2 is mounted at a predetermined position within the sample processing unit 10b of the soft mass analysis device 3 (see FIG. 2B). The measurement sample S1 and the reference sample S2 are precisely identical substances to each other in terms of molecular component and molecular structure. For example, the measurement sample S1 and the reference sample S2 are obtained by dividing single substance.

The control device 8 of FIG. 1 is constructed using a computer. Specifically, the control device 8 includes a CPU (Central Processing Unit/Central Processing and Control Unit) 17, a memory 18, a NIST (National Institute of Standards and Technology) table 19, and an ionization efficiency table 21. The CPU17 performs, as is well known, computations by means of computer for realizing various functions, and controls the operations of various units in the computer. The memory 18 is a storage medium for storing various pieces of information in a predetermined processing format, and is comprised of mechanical memory or semiconductor memory. The memory 18 includes also RAM (Random Access Memory) and ROM (Read Only Memory) that are internal memories of computer. The processing performed by the CPU17 may be done using a RAM as a temporary storage region.

Figure 3:
FIG. 3 is a view illustrating an example of storage content of a reference database.
Figure 3:
Figure 3:
Figure 3:

In the interior of the memory 18, provided are program software for executing qualitative analysis to be described later, a file area for storing various data, and a memory area for storing various data. The NIST table 19 is a well-known data table made by storing mass spectrums which are obtained by mass analysis having been conducted after ionizing various substances through EI process. In the table, mass spectrums of the order of 1.30 million (1,300,000) of compounds made of single component rather than mixtures are stored. For example, as illustrated in FIG. 3, m/z (mass-to-charge ratio), compound names, and EI mass spectrums are stored being associated with one another. Examples of data corresponding to (m/z)=78, 92 and 106 are shown in FIG. 3.

Figure 4:
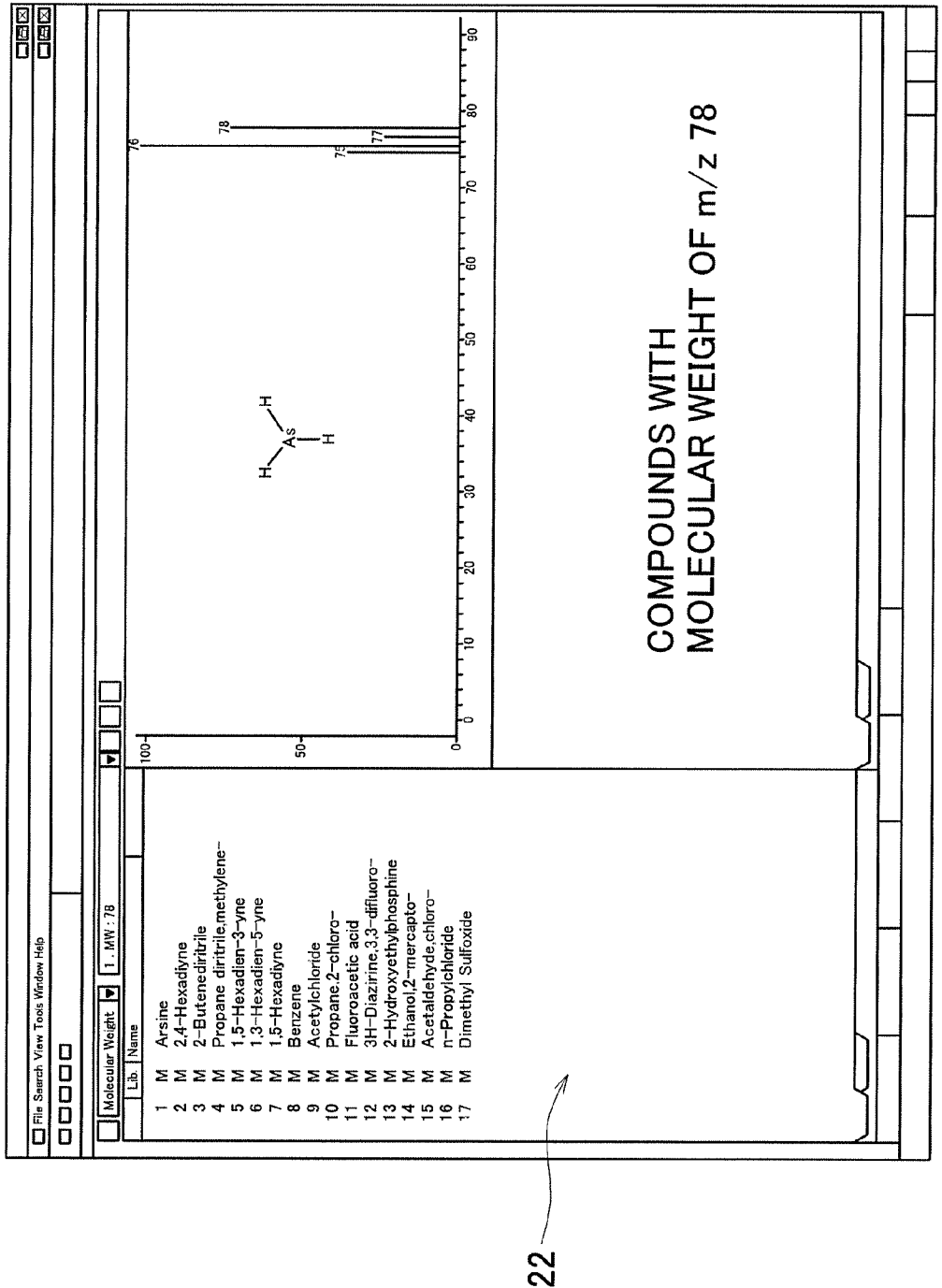
FIG. 4 is a view illustrating an example of search screen based on the database of FIG. 3.

For example, in FIG. 1, when we search compounds of (m/z)=78 by operating an input device 7 through CPU17 into NIST table 19, a search result as illustrated in FIG. 4 is obtained, which is displayed on a screen of an image display device 4. If we indicate (m/z)=78, as illustrated on a left column 22 of FIG. 4, 17 kinds of compounds including arsine and benzene of FIG. 3 will be listed as compounds that fit into (m/z)=78. Normally, a plurality of compounds will be also listed for other (m/z) values.

Figure 5:
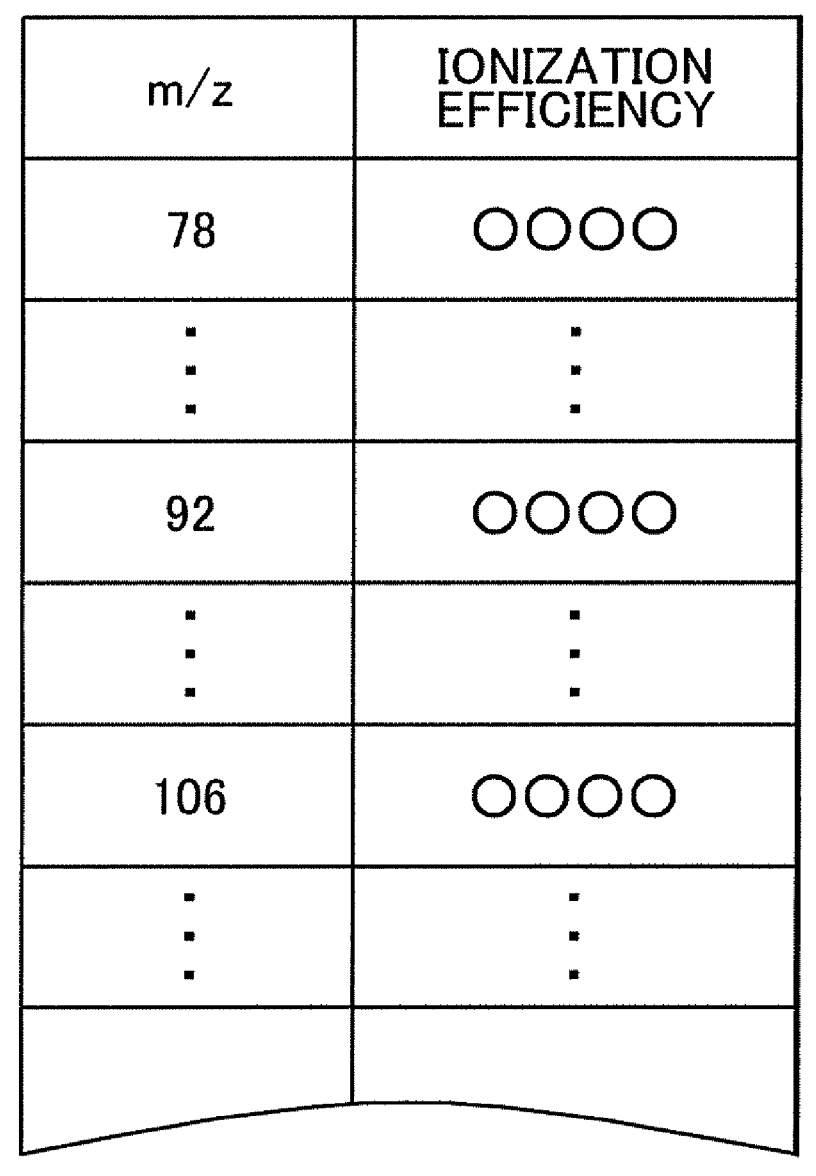

In an ionization efficiency table 21 of FIG. 1, for example, as illustrated in FIG. 5, ionization efficiencies corresponding to various compounds are stored for each (m/z). These values of ionization efficiencies are obtained beforehand through experiments, or literature values.

Figure 6:
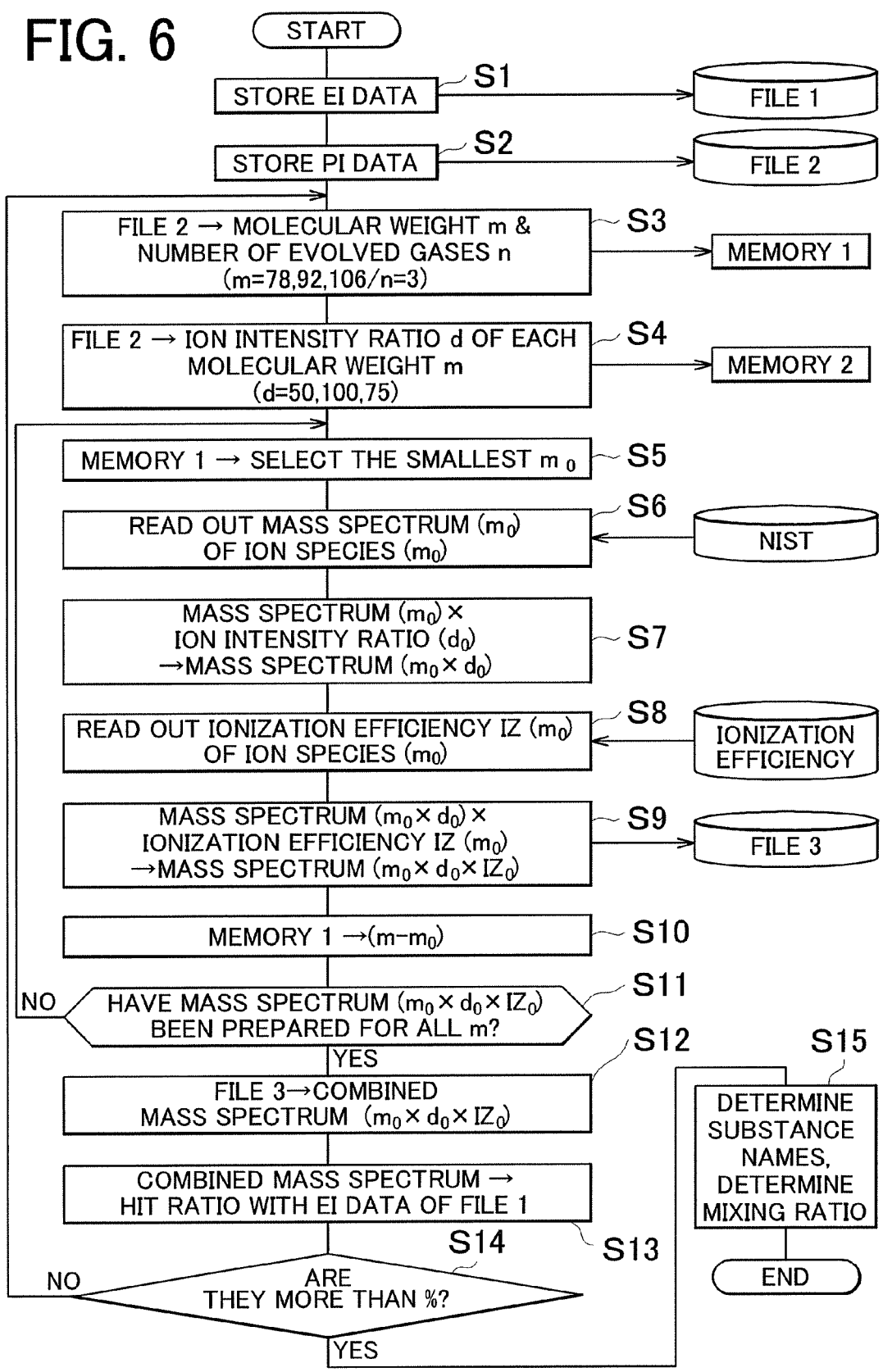
FIG. 6 is a flowchart illustrating an embodiment of a gas analyzing method according to the present invention.

Hereinafter, a gas analyzing method implemented by the gas analyzing apparatus 1 that is formed of the above configuration will be described now with reference to a flowchart as illustrated in FIG. 6. It is to be noted that, though the present embodiment may take various gases as measurement target, mixed gases with component consisting of three molecules of benzene (m/z=78), toluene (m/z=92), and xylene (m/z=106) will be taken as measurement target, in order to facilitate understanding. As a matter of course, it has not been known that the above three substances are contained in the mixed gases before the completion of the analysis. In the present embodiment, soft ionization is to be performed through PI (photo-ionization) process.

Referring now to FIG. 1, an operator firstly makes a reference sample S2 by dividing an unknown sample S1. Then, the operator sets the unknown sample Si at a predetermined position of a sample processing unit 10a of an EI mass analysis device 2 (see FIG. 2A), and sets the reference sample S2 at a predetermined position of a sample processing unit 10b of a soft mass analysis device 3 (see FIG. 2B). Then, the operator activates a temperature regulator incorporated in the both devices, to perform temperature control in such a manner that the measurement sample S1 and the reference sample S2 exhibit exactly the same temperature change. When this temperature change develops, thermal changes occur in the samples S1 and S2, which causes gas to be evolved. In the present embodiment, an analysis is conducted to determine components of gas that has evolved from the measurement sample S1. That is, qualitative analysis is conducted.

Figure 7A:
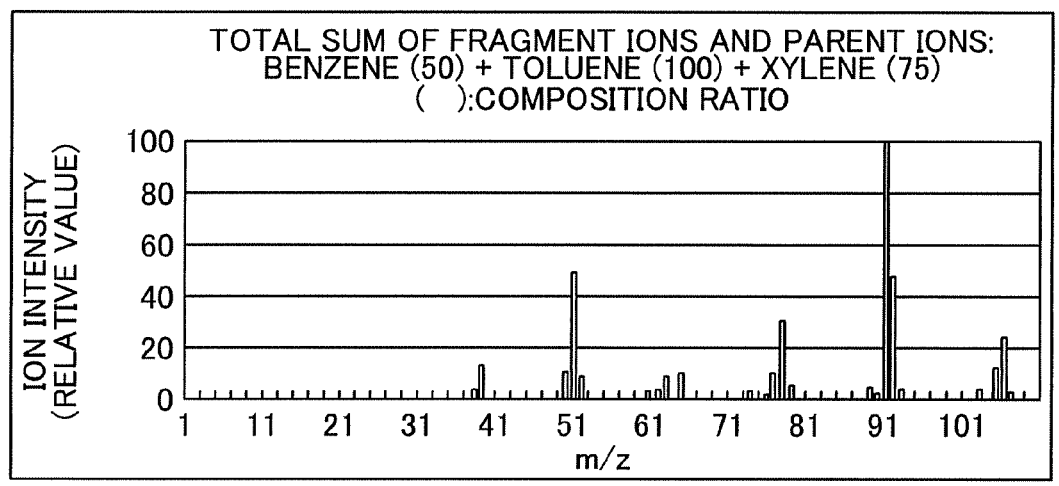
FIGS. 7A and 7B illustrate an example of measurement data obtained during processing of FIG. 6, FIG. 7A illustrating EI measurement data and FIG. 7B illustrating PI measurement data, respectively.
Figure 7B:
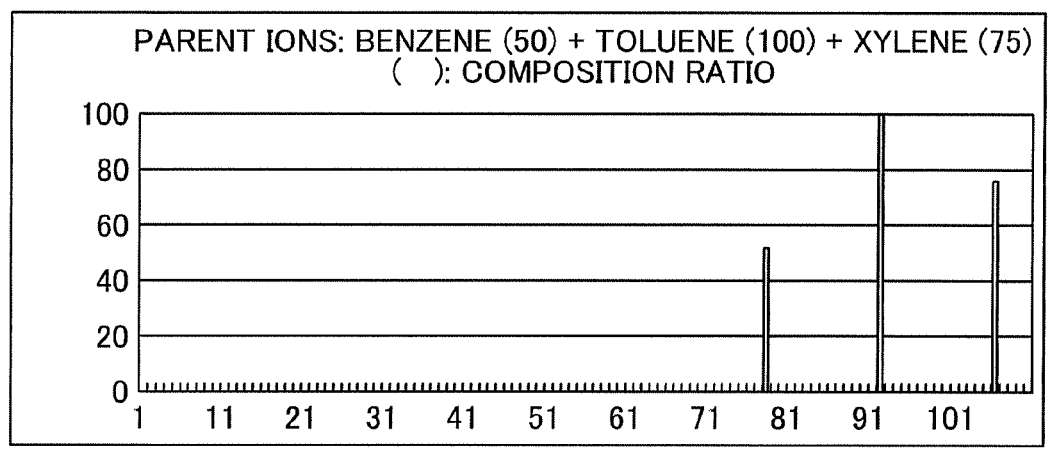

Gas evolved from the measurement sample S1 is subjected to mass analysis based on EI process, while gas evolved from the reference sample S2 is subjected to mass analysis based on PI process. For example, through the EI mass analysis, mass spectrum as illustrated in FIG. 7A is obtained as measurement result. In the mass spectrum, although the values of (m/z) of respective components of benzene, toluene and xylene are 78, 92 and 106 respectively, fragment ions inherent in EI process are generated depending on their molecular structures of respective components, so that ion peaks appear over a wide range of (m/z). On the other hand, mass spectrum as illustrated in FIG. 7B, for example, is obtained as measurement result through PI mass analysis conducted by means of the PI mass analysis device 3 of FIG. 1. In PI, since fragment ions are not generated, but only parent ions are generated, parent ions of three kinds of (m/z)=78, 92 and 106 appear.

In step S1 of FIG. 6, the CPU 17 of FIG. 1 stores EI measurement data of FIG. 7A in a file 1. Also, in step S2, the CPU 17 stores PI measurement data of FIG. 7B in a file 2. Next, in step S3, the CPU 17 determines (m/z)=78, 92 and 106 of evolved gases from the PI measurement data of FIG. 7B stored in the file 2, and further determines the number of evolved gases to be three, then stores them in the memory. At this time, the substance names of evolved gases remain unknown. Further, in step S4, the CPU 17 determines ion intensity ratios "d" of component molecules of evolved gases from the PI measurement data of FIG. 7B stored in the file 2. In the present embodiment, the ion intensity ratios "d" of (m/z)=78, 92 and 106 were 50, 100 and 75, respectively. The ion intensity ratio means a concentration ratio of each component molecule to the entire mixture.

Figure 8A:
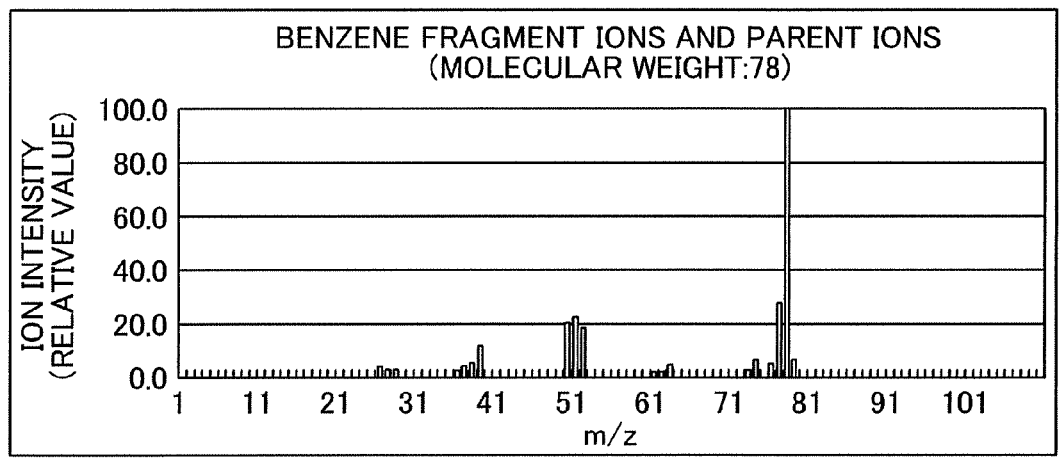
FIGS. 8A and 8B are views illustrating an example of data stored in the database of FIG. 3 in a form of mass spectrum, FIG. 8A illustrating that of benzene and FIG. 8B illustrating that of toluene, respectively.

Next, in step S5, the CPU 17 selects the smallest (m/z), i.e. 78, among three values of (m/z), and further in step S6, reads out NIST data corresponding to the ion species having the same (m/z) value from NIST table 19 as mass spectrum data for reference. At this time, mass spectrum (m/z=78) of benzene as illustrated in FIG. 8A as well as the other multitude of compounds being determined as (m/z)=78 are searched and selected from the NIST table 19.

Next, in step S7, a multitude of reference data that have been read out are multiplied by ion intensity ratio "d" corresponding to (m/z)=78. While NIST data have been standardized in value, actual evolved gases have intensities varying among respective molecular components as shown in FIG. 7B. The reason that reference data are multiplied by ion intensity ratio "d" is to compensate the difference of intensity for each molecular component.

Next, in step S8, ionization efficiencies "IZ" of substances of (m/z)=78 are read out from the ionization efficiency table 21 of FIG. 1. Further, in step S9, NIST data are multiplied by the ionization efficiencies. While NIST data have been standardized in value, actual evolved gases have ionization efficiencies varying among respective molecular components. The reason that NIST data are multiplied by the ionization efficiencies is to compensate the difference of ionization efficiency for each molecular component.

Through the above steps, reference data relating to molecules of (m/z)=78 are obtained, and these data are stored in the file 3. Then, (m/z)=78 for which processing has been completed is deleted from (m/z) values stored in the memory 1 in step S3 (step S10). Then, in step S11, the CPU17 determines whether or not processes have been completed for all component molecules, and if they have not completed (namely, "NO" in step S11), then returning to step S5, and repeats processing to generate EI data for reference (step S9) for the remaining (m/z)=92, 106.

Figure 8B:
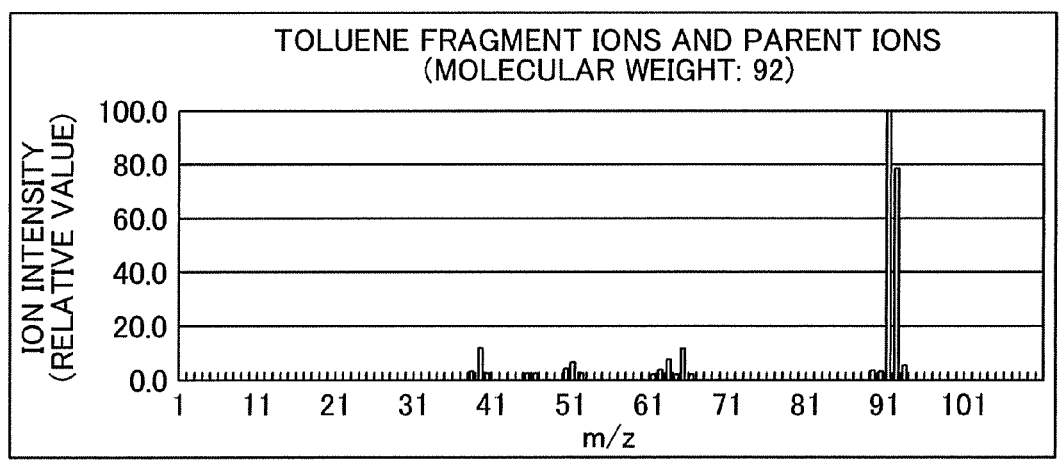
Figure 9A:
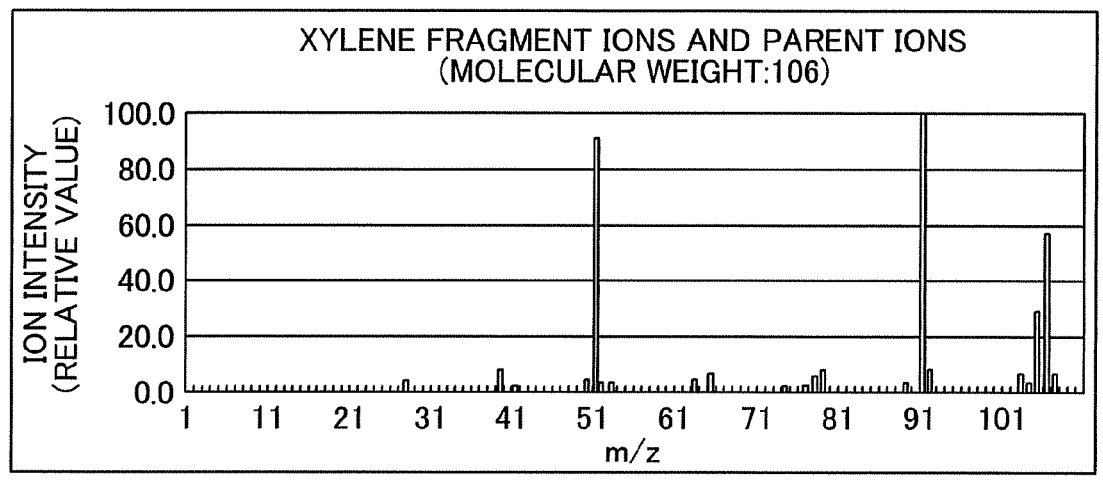
FIG. 9A is a view illustrating mass spectrum of xylene stored in the database of FIG. 3.

In these processes, processing will be carried out for toluene of (m/z)=92 as illustrated in FIG. 8B as well as other molecules which are equivalences of (m/z)=92. Then, further, processing will be carried out for xylene of (m/z)=106 as illustrated in FIG. 9A as well as other molecules which are equivalences of (m/z)=106. Then, when processing is completed for up to final (m/z), all EI data for reference corresponding to (m/z)=78, 92 and 106 are accumulated in the file 3 in step S9.

Figure 9B:
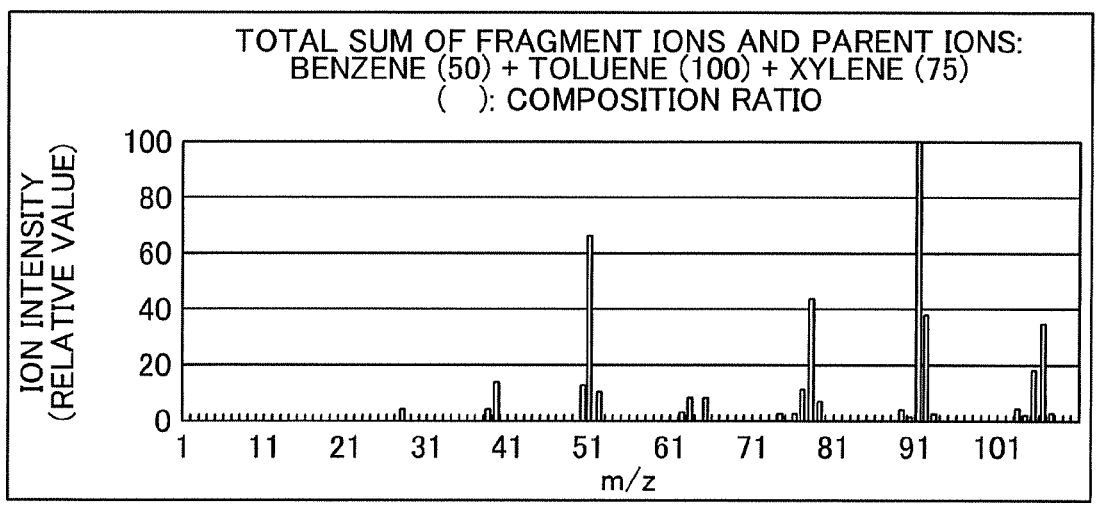
FIG. 9B is a view illustrating combined mass spectrum generated during processing of FIG. 6.

Subsequently, in step S12, the CPU17 combines three types of EI data of (m/z)=78, 92 and 106 accumulated in the file 3 of step S9 on one-by-one basis. An example of the combined results may be mass spectrum, for example, as illustrated in FIG. 9B. Later, the combined EI data are compared with EI measurement data (see FIG. 7A) stored in the file 1 in step S1. Specifically, the CPU17 compares the above data in terms of (m/z) value and ion intensity in accordance with a well known predetermined algorithm to calculate hit ratio (%) which depicts how much the data of mass spectrums coincide with each other. Then, if the hit ratio (%) is not less than a predetermined value, the CPU17 determines three types of substance names and mixing ratio constituting combined EI data at this time as analysis result itself or candidates for analysis result.

As described above, according to the present embodiment, molecules contained in EI measurement data are to be determine by repeating the following processes: estimating parent ions in evolved gases (step S3); reading out (steps S5 to S11) NIST data of estimated parent ions; combining NIST data for each of read out component molecules, and subsequently comparing the combined data with EI measurement data (steps 12 to 14).

According to the method, EI measurement data obtained through measurements are not directly compared with enormous volumes of NIST data. Instead, after decreasing NIST data in number by effectively utilizing the data of molecular weights and the number of evolved gases that have been obtained through PI measurement data, the decreased NIST data are compared with EI measurement data. Thus, determination result that is finally obtained is very accurate, and the data to be calculated can be greatly reduced in number, and moreover, memory capacity and time length for computation processing can be greatly reduced.

Second Embodiment of Gas Analyzing Method and Gas Analyzing Apparatus

Figure 10:
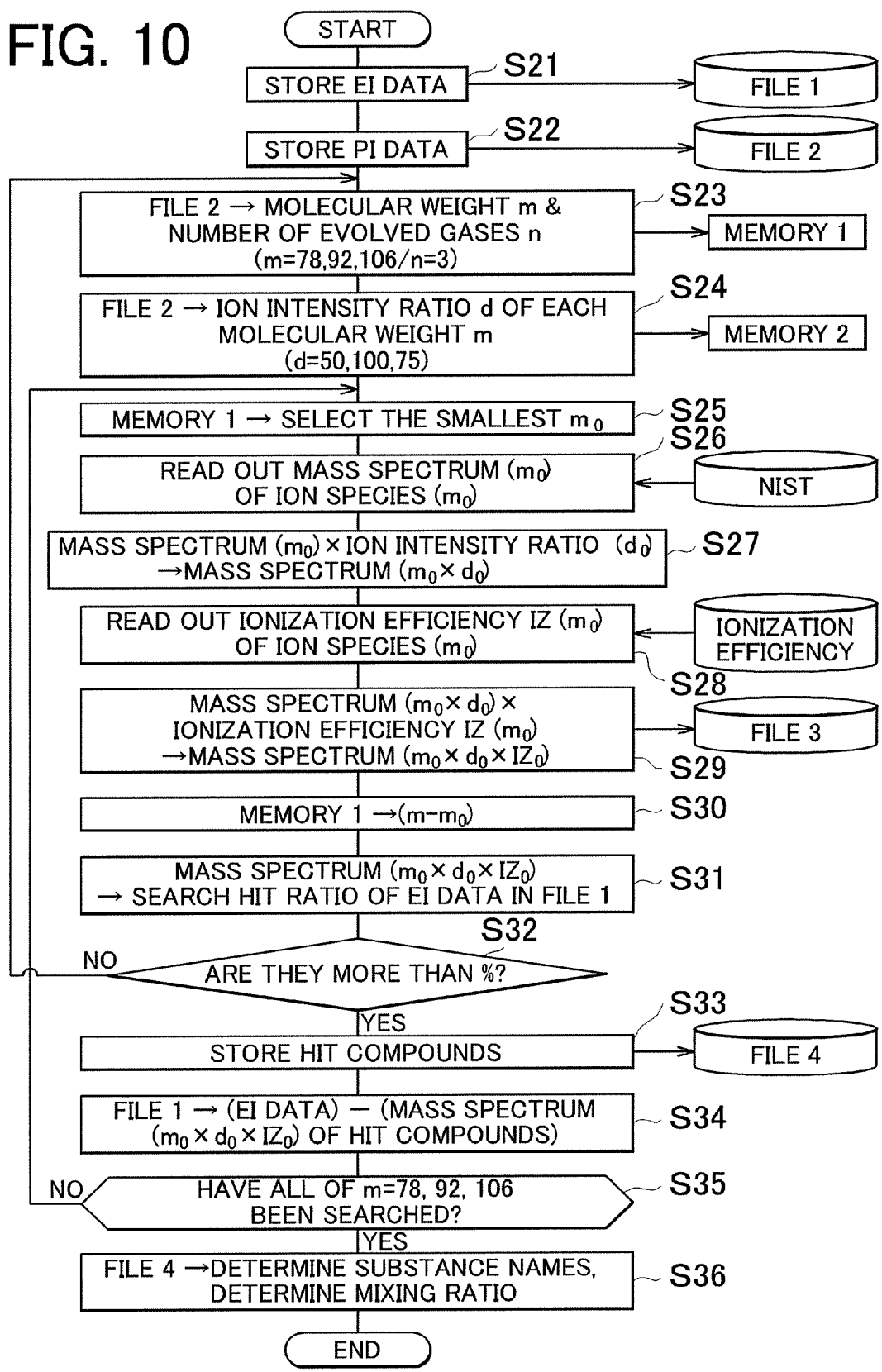
FIG. 10 is a flowchart illustrating another embodiment of a gas analyzing method according to the present invention.

FIG. 10 is a flowchart illustrating a main part of another embodiment of a gas analyzing method and a gas analyzing apparatus according to the present invention. The mechanical configuration of the embodiment is the same as that of the earlier embodiment as illustrated in FIG. 1, FIG. 2A and FIG. 2B. What is different between them is a process realized by means of a qualitative analysis program stored in the memory 18. The process will now be described.

In the present embodiment, various samples also may be measurement targets, but in the following description, in order to facilitate understanding, mixed gases having the components made up of three molecules of benzene (m/z=78), toluene (m/z=92), and xylene (m/z=106) are taken as measurement targets. As a matter of course, it is not known that the above-mentioned three substances are contained in the mixed gases before the completion of the analysis. In the present embodiment, soft ionization is also to be performed through PI (photo-ionization).

As described in the earlier embodiment as shown in FIG. 1, EI measurement data (see FIG. 7A) is obtained by means of the EI mass analysis device 2. On the other hand, PI measurement data (see FIG. 7B) is obtained by means of the PI mass analysis device 3. The EI measurement data contains fragment ions, while PI measurement data contains only parent ions without containing fragment ions.

In step S21 of FIG. 10, the CPU17 of FIG. 1 stores EI measurement data of FIG. 7A in the file 1. In step S22, the CPU17 stores PI measurement data of FIG. 7B in the file 2. Next, in step S23, the CPU17 determines (m/z)=78, 92 and 106 of evolved gases from the PI measurement data of FIG. 7B stored in the file 2, and further, the CPU17 determines the number of evolved gases to be three, and stores them in the memory. At this time, it is impossible to know up to substance names of evolved gases. Further, in step S24, the CPU17 determines ion intensity ratios "d" of component molecules of evolved gases from the PI measurement data of FIG. 7B stored in the file 2. In the present embodiment, ion intensity ratios "d" of (m/z)=78, 92 and 106 were 50, 100 and 75, respectively. The ion intensity ratio means concentration ratio of each component molecules to the entire mixture.

Next, in step S25, the CPU17 selects the smallest (m/z) value of 78 among three (m/z) values, and further in step S26, reads out NIST data corresponding to ion species having the same (m/z) value from NIST table 19 as mass spectrum data for reference. At this time, from NIST table 19, searched are mass spectrums (m/z=78) of benzene as illustrated in FIG. 8A, and other than this, a multitude of compounds that have been determined as (m/z)=78.

Next, in step S27, the CPU17 multiplies a multitude of read out reference data by ion intensity ratios "d" corresponding to (m/z)=78. While NIST data have been standardized in value, actual evolved gases have intensities varying among respective molecular components as shown in FIG. 7B. The reason that reference data are multiplied by ion intensity ratio "d" is to compensate the difference of intensity for each molecular component.

Next, in step S28, ionization efficiencies "IZ" of substances of (m/z)=78 are read out from ionization efficiency table 21 of FIG. 1, and further, in step S29, NIST data are multiplied by the ionization efficiencies. While NIST data have been standardized in value, actual evolved gases have ionization efficiencies varying among respective molecular components. The reason that NIST data are multiplied by the ionization efficiencies is to compensate the difference of ionization efficiency for each molecular component.

Through the above steps, reference data relating to molecules of (m/z)=78 is generated, and these data are stored in the file 3. Then, the CPU17 deletes (m/z)=78 for which processing has been completed among (m/z) values stored in the memory 1 in step S3 (step S30). Then, in step S31, the CPU17 calculates hit ratio of individual data of a plurality of reference data relating to molecules of (m/z)=78 to EI measurement data stored in the file 21 of step S21. The hit ratio is calculated by comparing EI measurement data with reference data in terms of (m/z) value and ion intensity in accordance with a well known predetermined algorithm. If there is any compound with hit ratio of not less than a predetermined hit ratio in a plurality of reference data, the CPU17 stores its compound names in a file 4 in step S33.

This search processing is performed for all compounds that have been read out based on (m/z)=78. When this processing is completed, in step S34, the CPU17 subtracts mass spectrums of all hit compounds stored in the file 4 from EI measurement data in the file 1 of step S21. Thereby, reference data can be reduced in number when executing search processing for compounds corresponding to the remaining (m/z)=92, 106.

A search algorithm of mass spectrums generally performs profile fitting using signals with high ion intensity and signals with large molecular weights. As a result, when mixed gases are to be analyzed, it becomes hard to distinguish component with small molecular weight from fragment with large molecular weight, so that it is hard to perform an accurate qualitative analysis. Contrary to this, as with the present embodiment, if we make it a rule to execute search processing in the order of molecule with the smallest (m/z) first, it becomes possible that searches can be surely targeted for molecule components which used to be hardly caught by searching owing to small molecular weights thereof.

Through the above steps, search with respect to the molecules of (m/z)=78 is completed, the result of which is stored in a file 4, and subsequently, search is executed in the same way for molecules of the remaining (m/z)=92, 106 ("NO" in step S35 to S34). As a result, molecules of (m/z)=92, 106 with high hit ratio is stored in the file 4. After searching process is completed for all component molecules ("YES" in step S35), then in step 36, the CPU17 determines molecule names and mixing ratios stored in the file 4 as analysis result itself or analysis result candidate.

As described above, according to the present embodiment, it was designed to determine what component molecules contained in EI measurement data are by repeating the following processes: estimating parent ions in evolved gases (step S23); reading out NIST data of estimated parent ions (steps S25 to S30); comparing the NIST data for each read-out component molecule with EI measurement data (step 31).

According to the method, EI measurement data obtained through measurements are not directly searched from enormous volumes of MIST data, but NIST data is compared with EI measurement data in a state that NIST data has been narrowed down in advance by making effective use of the data of molecular weights and the number of evolved gases that have been obtained through PI measurement data. For this reason, determination result that is finally obtained is very accurate, and the number of data that will be targets of computation can be greatly reduced, and moreover, memory capacity and a time length for computation processing can be greatly reduced.

Third Embodiment of Gas Analyzing Method and Gas Analyzing Apparatus

Figure 11:
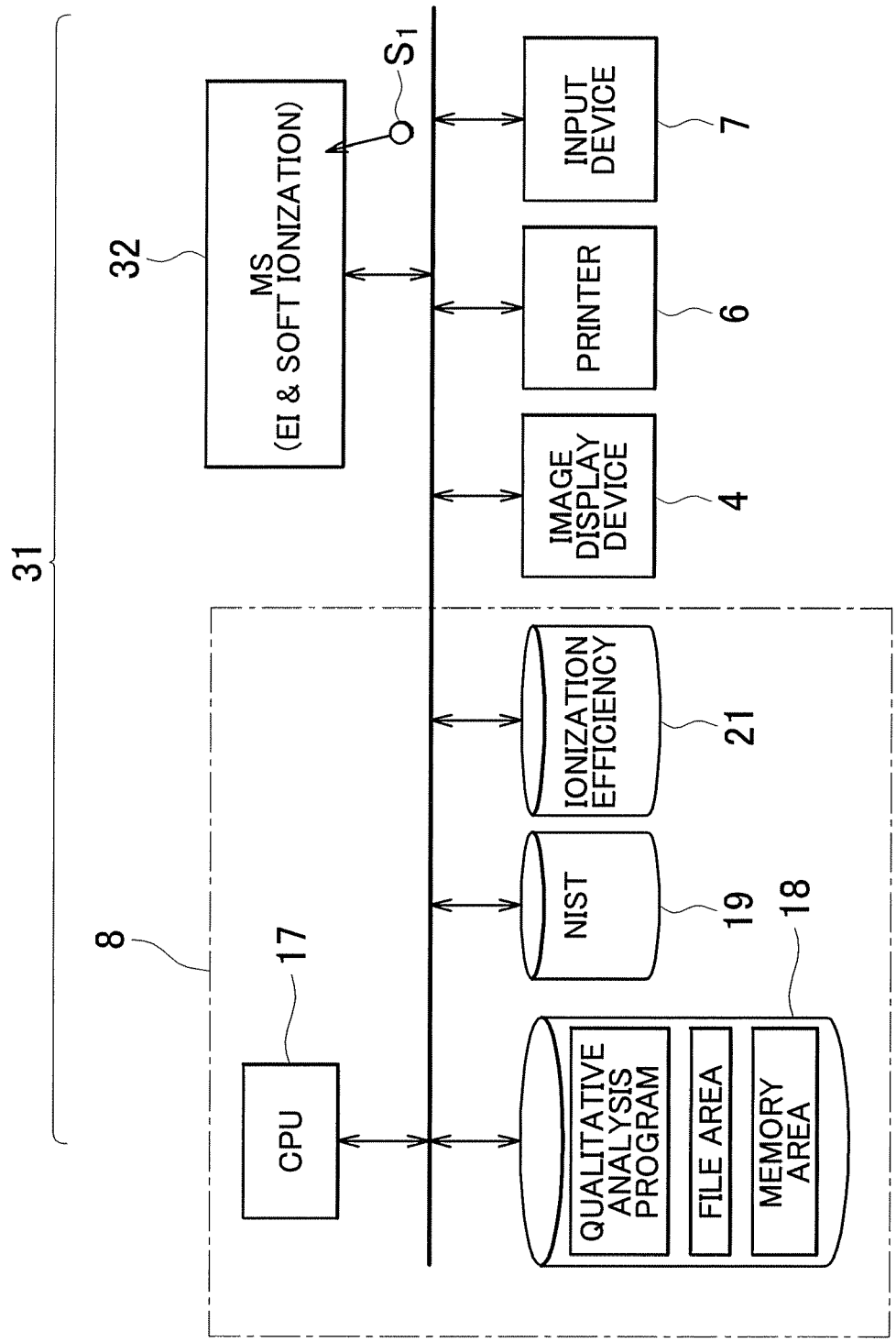
FIG. 11 is a block diagram illustrating another embodiment of a gas analyzing apparatus that implements a gas analyzing method according to the present invention.

FIG. 11 illustrates a still another embodiment of a gas analyzing apparatus for implementing a gas analyzing method according to the present invention. The point that a gas analyzing apparatus 31 as illustrated here is different from a gas analyzing apparatus 1 as illustrated in FIG. 1 is to have added modification to a mass analysis device 32. The embodiment will be described in detail. The elements shown with the similar reference numerals to those of FIG. 1 are the similar elements, and will not be described any further.

Figure 12:
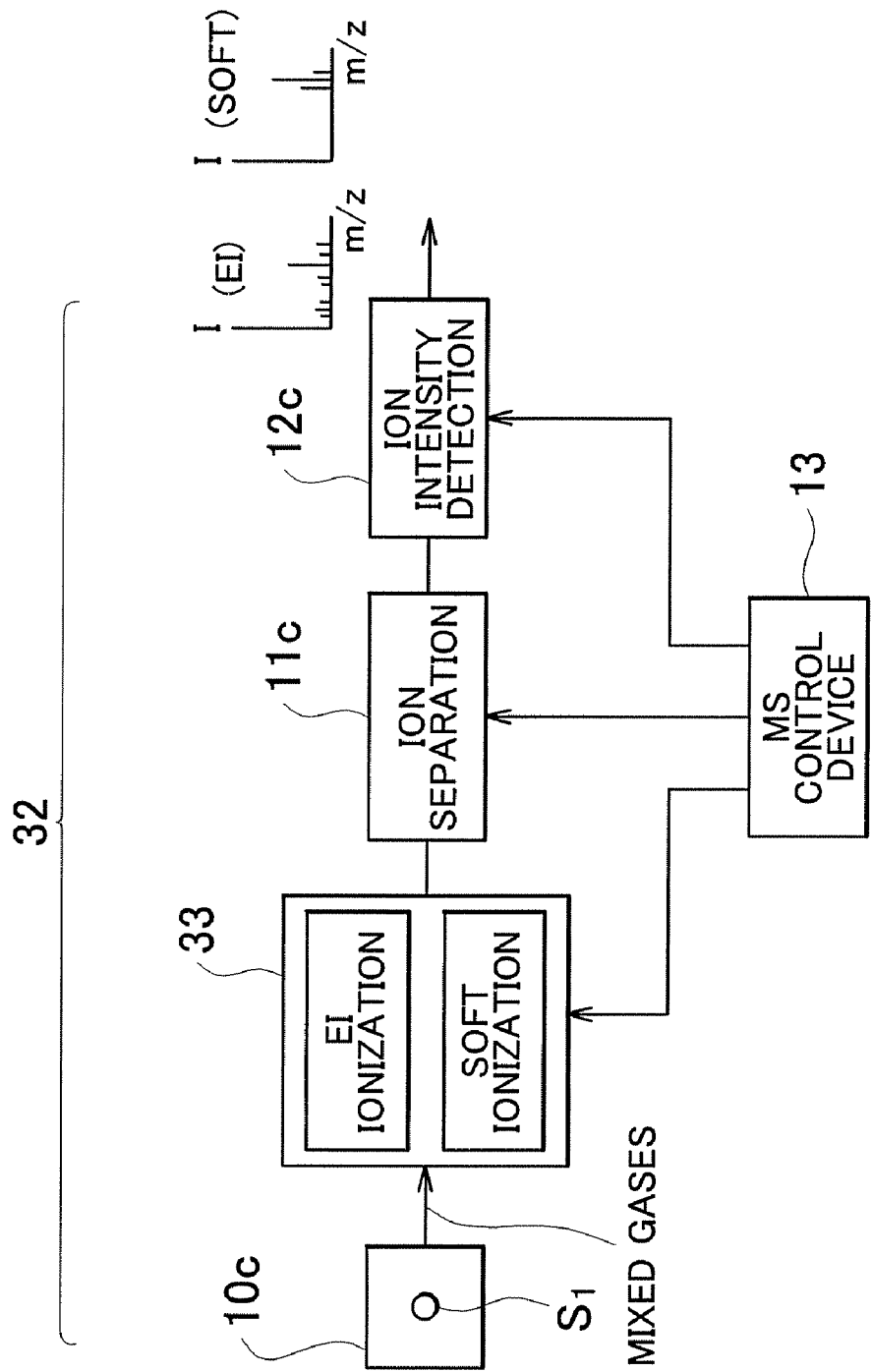
FIG. 12 is a view illustrating a mass analysis device that is a main part of device of FIG. 11.

In a gas analyzing apparatus 1 shown in FIG. 1, an EI mass analysis device 2 and a soft mass analysis device 3 are installed as separate devices. In contrast, in the present embodiment, an EI mass analysis device and a PI mass analysis device are configured by one mass analysis device 32. A sample S1 being a measurement target is set at a predetermined position in the inside of the mass analysis device 32. The mass analysis device 32 has, for example, as illustrated in FIG. 12, a sample processing unit 10c, an ionization device 33, an ion separation device 11c, and an ion intensity detection device 12c. The ion separation device 11c and the ion intensity detection device 12c have the similar configuration to those of the ion separation device 11a and the ion intensity detection device 12a used in the EI mass analysis device 2.

The sample processing unit 10c has any desired structure in which a sample can be fixedly arranged, in a similar manner to the sample processing unit 10a of the EI mass analysis device 2 of FIG. 2A, and further has a temperature regulator around the location where samples are arranged. The temperature regulator has a heater and a cooler as needed, and causes temperatures of sample S2 to rise and to decrease as needed in accordance with a predetermined program. The ionization device 33 has the both of the EI device and the soft ionization device (for example, PI device) within a casing. If gas is introduced into the casing and the EI device is activated, gas can be ionized through the EI process, while if gas is introduced into the casing and the soft ionization device is activated, gas can be ionized through the soft ionization process.

Normally, EI measurement data and soft ionization measurement data can be obtained from one evolved gas by selectively activating the EI device and the soft ionization device at different short period of times. Note that the different short period of times may be realized by dividing an appropriate length of time into two, or may be short period of times in which EI process and soft ionization process are repeated alternately within an appropriate length of time. With the above-mentioned configuration, the EI measurement data and the soft ionization measurement data (for example, PI measurement data) are obtained separately at an output terminal of the ion intensity detection device 12c. Thus obtained EI measurement data and soft ionization measurement data are subjected to processing as shown in FIG. 6 or FIG. 10, and hence substance names and mixing ratios of component molecules contained in evolved gas are determined. Thus, qualitative analysis is performed for evolved gases. According to the embodiment, both of the EI measurement data and the soft ionization measurement data are obtained from single evolved gas, and thereby qualitative analysis on evolved gases can be conducted accurately in real time.

Fourth Embodiment of Gas Analyzing Method and Gas Analyzing Apparatus

Figure 13:
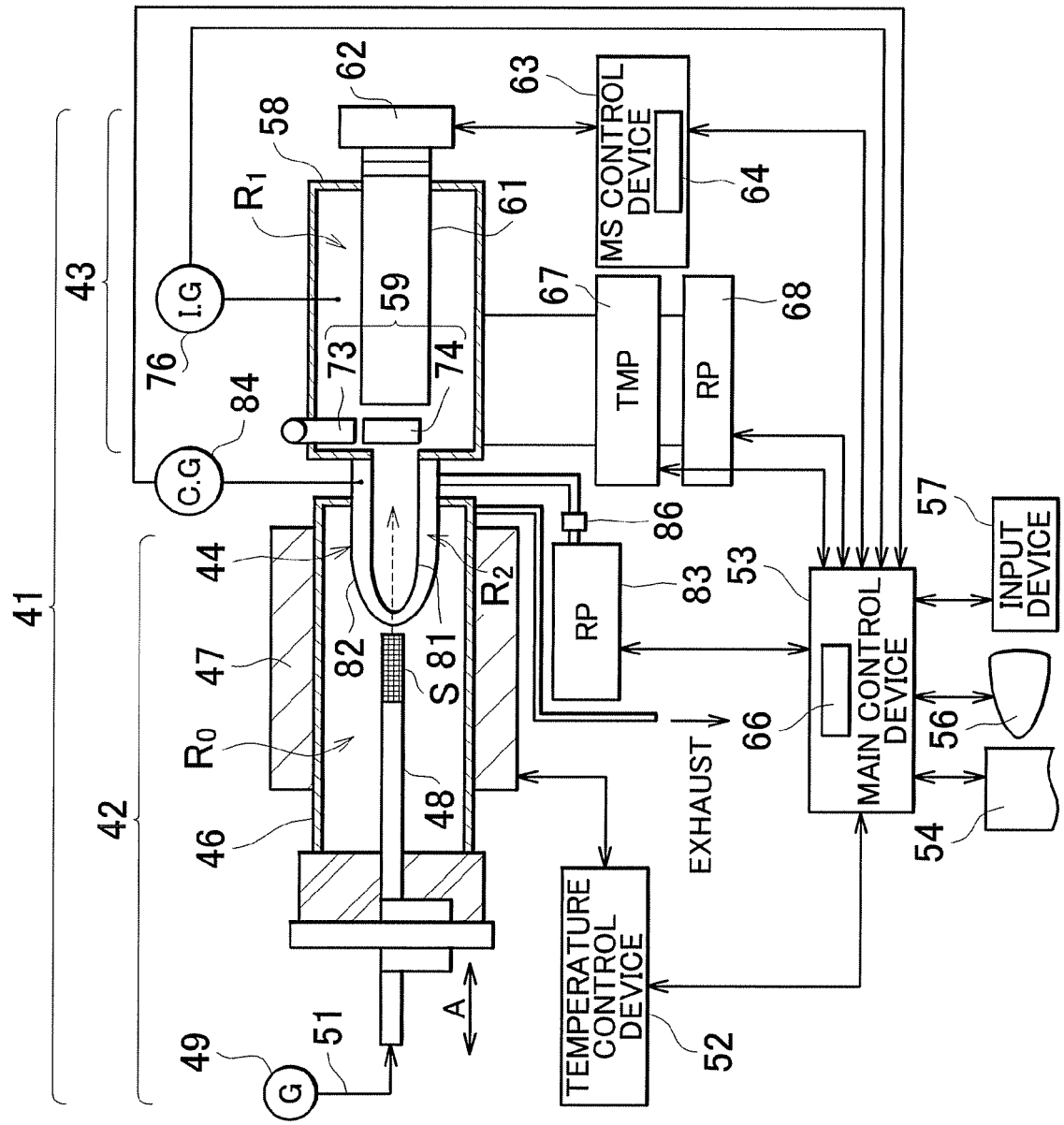
FIG. 13 is a view illustrating a still another embodiment of a gas analyzing apparatus according to the present invention.
Figure 14:
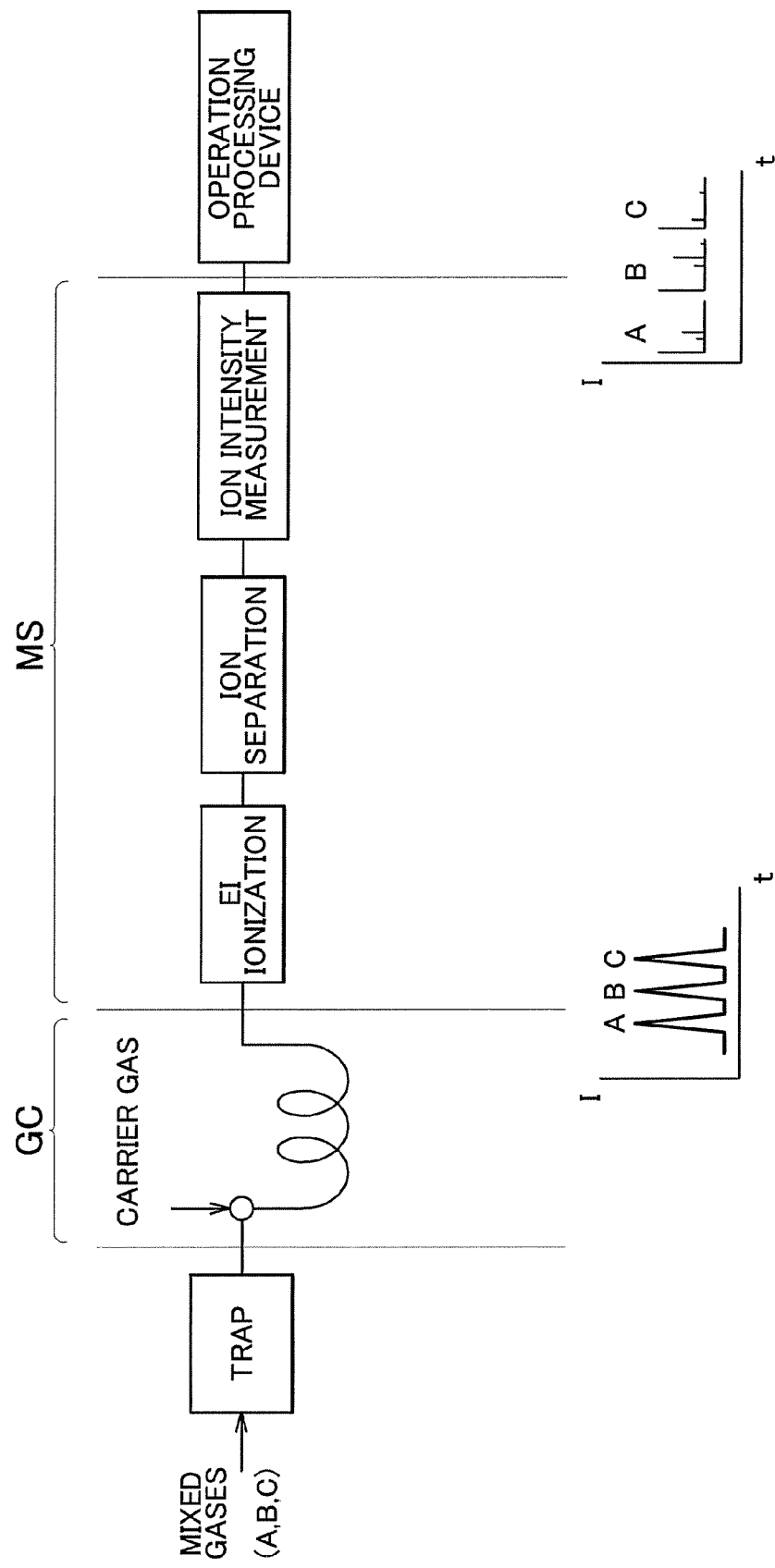
FIG. 14 is a view illustrating an example of a conventional gas analyzing apparatus.
Figure 15:
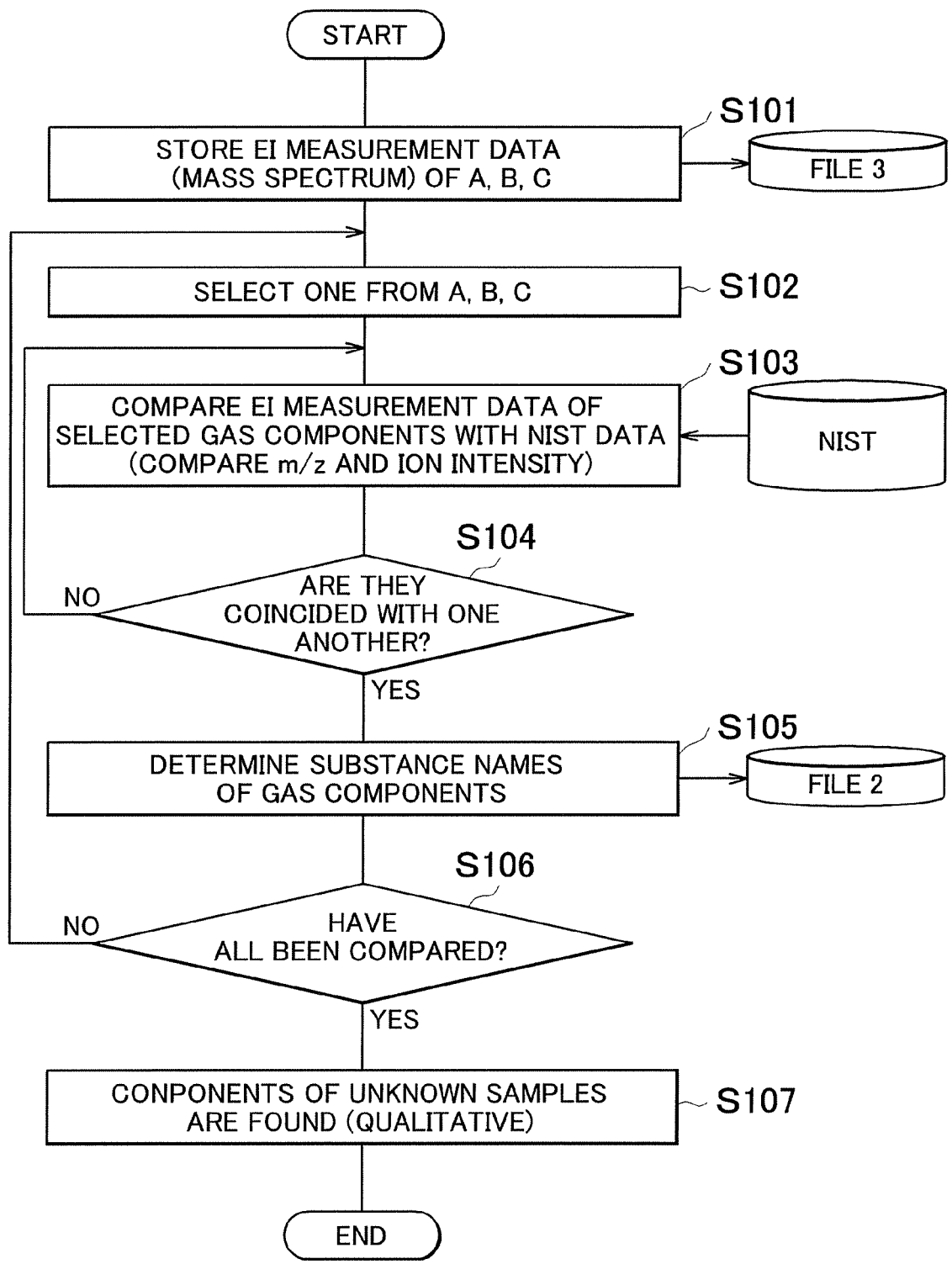
FIG. 15 is a flowchart illustrating an example of processing executed by the apparatus of FIG. 14.

FIG. 13 illustrates still another embodiment of a gas analyzing apparatus for implementing a gas analyzing method according to the present invention. The gas analyzing apparatus 41 is a known apparatus disclosed in FIG. 1 of PCT Publication WO2007/108211 pamphlet. The gas analyzing apparatus 41 is suitable for realizing an embodiment as shown in FIG. 11, which carries out the both of the EI process and the soft ionization process by means of one mass analysis device 32.

Structure of the gas analyzing apparatus 41 is described in detail in the foregoing PCT Publication pamphlet, and accordingly will not be described in detail any further. If we give an outline, however, the gas analyzing apparatus 41 has a temperature programmed desorption analyzer 42 being a gas generation device as a sample processing unit, and an analysis device 43 that executes gas analysis. The temperature programmed desorption analyzer 42 and the analysis device 43 are connected to each other by means of a gas conveyor 44.

The temperature programmed desorption analyzer 42 is a device used as a gas generation unit for conducting thermal analysis based on the thermal desorption technique spectroscopy. The thermal desorption technique spectroscopy is an analytical method for finding a gas absorption amount or a gas absorption state from analysis of desorption process when the temperature of the surface of a solid sample on which a gas is absorbed is increased. The temperature programmed desorption analyzer 42 has a casing 46 forming a sample chamber R0, a heating furnace 47 serving as a heating means provided in the surroundings of the casing 46, and a sample tube 48 fitted to the casing 46. The sample tube 48 can be removably inserted in the casing 46 as indicated by an arrow A.

The sample tube 48 supports a sample S at its tip. A gas supply source 49 is connected via a piping 51 to a rear portion of the sample tube 48. The gas supply source 49 emits a carrier gas, e.g., inert gas, e.g., Helium (He) gas. The heating furnace 47 comprises a heating device that employs a heat-generating wire as a heat source, which generates heat when an electric current is applied thereto. The heating furnace 47 generates heat in response to a command from a temperature control device 52. When the sample chamber R0 is required to be cooled, a cooler is additionally provided to the sample chamber R0. The temperature controller 52 includes a computer, a sequencer, a dedicated circuit, or the like. A software program for increasing temperature is stored in a storage medium in the temperature control device 52.

The temperature control device 52 operates in response to a command from a main control device 53. The main controller 53 includes a computer, for example. A printer 54, a display 56 and an input device 57 are connected to the main controller 53 via input/output interfaces.

The analysis device 43 includes a casing 58 forming an analysis chamber R1, an ionization device 59 provided in the analysis chamber R1, a quadrupole filter 61 as ion separation means, an ion detection device 62, and a mass analysis control device 63. The mass analysis control device 63 is connected to the main control device 53 to control operations of respective elements including the ionization device 59, the quadrupole filter 61, and the ion detection device 62. The mass analysis control device 63 includes an electrometer 64 that arithmetically produce the intensity of an ion detected by the ion detector 62. The main control device 53 includes an arithmetic operating unit 66 for performing a predetermined arithmetic operation or calculation based on the ion intensity calculated by the electrometer 64. The arithmetic operating unit 66 is configured of, for example, a combination of an operating and controlling device of a computer and software of a computer.

The casing 58 is additionally provided with a turbo molecular pump 67 and a rotary pump 68. The rotary pump 68 roughly reduces the pressure in the analysis chamber R1. Then, the turbo molecular pump 67 further reduces the pressure in the analysis chamber R1 which has been roughly reduced by the rotary pump 68 to vacuum or to a depressurized state close to vacuum. A pressure within the analysis chamber R1 is detected by means of an ion gauge 76, which is a pressure gauge. Then, the detection results of the ion gauge 76 are sent as an electric signal to the main control device 53.

The quadrupole filter 61 includes four rod-like electrodes (not shown). A scanning voltage is applied to the electrodes. The scanning voltage is formed by superposing a high-frequency alternating voltage whose frequency changes with the passage of time and a predetermined magnitude of a direct-current voltage to each other. With this high-frequency scanning voltage being applied to the quadrupole electrodes, ions passing among these quadrupole electrodes are separated for each mass-to-charge ratio of molecules, namely every mass-to-charge ratio. Then, each ion as thus separated is introduced into the ion detector 62 provided downstream, or behind.

The ion detection device 62 includes an ion deflector and an electron multiplier tube (either of these two is not shown). Ions that have been selected by the quadrupole filter 61 are collected by the ion deflector to the electron multiplier tube, and subsequently output as an electric signal. The signal is counted by the electrometer 64 and is output as an ion intensity signal.

The ionization device 59 includes a lamp 73 for PI (Photo-ionization) as a light emitting means, and an EI (Electron Ionization) device 74. The lamp 73 is securely fixed to the casing 58 so as to pass through it. The portion of the casing 58 to which the lamp 73 is fixed is sealed with a sealing member in an airtight manner. A light-emitting surface of the lamp 73 faces the EI device 74. The end portion of the lamp 73, which is opposite to the light-emitting surface thereof, is positioned outside of the casing 58.

The EI device 74 has a filament (not shown) serving as electron emitting means for emitting electrons when an electric current is applied thereto, an external electrode (not shown) that surrounds the filament, and an internal electrode (not shown) that is paired with the external electrode. The external electrode and the internal electrode both have a structure capable of transmitting light. The structure may be formed, for example, in a mesh shape, in a spiral shape, or by using a translucent member.

In the EI device 74, the filament generates thermal electrons when an electric current is applied thereto, and the thermal electrons thus generated are accelerated by electric voltage applied between the external electrode and the internal electrode. When gas is introduced into the EI device 74, the thermal electrons collide with the gas to ionize the same. On the other hand, when the lamp 73 is turned on to emit light, the gas introduced into the EI device 74 is ionized by light in the condition of soft ionization. If eclectically energizing to the filament is stopped after the filament is eclectically energized during a predetermined period of time, and subsequently, the lump 73 is turned on to emit light during a predetermined period of time, then both EI and soft ionizations can be performed sequentially with reference to the gas introduced through one introducing process. Alternatively, the filament may be energized and stopped energizing alternately and repeatedly at a short time interval within a predetermined period of time, and the lamp 73 may be turned on and off alternately and repeatedly in synchronization with energizing the filament, so that both EI and soft ionizations can be performed sequentially with reference to the gas introduced through one introducing process.

The gas conveyor 44 includes an inner tube 81 for conveying the gas, an outer tube 82 surrounding the inner tube 81, and a rotary pump 83 serving as exhaust means that exhausts air from an intermediate chamber R2 formed between the outer tube 82 and the inner tube 81. A mass flow meter 86 is provided as flow-rate adjusting means in front of the rotary pump 83. With the exhaust operation of the rotary pump 83, the inside of the intermediate chamber R2 can be set at a pressure lower than that of the sample chamber R0. The pressure inside the intermediate chamber R2 is detected by means of a crystal gauge 84, which is a pressure gauge. The detection results are sent as an electrical signal to the main controller 53.

The mass flow meter 86 is an element that allows gas to flow between an exhaust path of the rotary pump 83 and an external pressure (atmospheric pressure in the present embodiment). For example, when atmospheric gas is introduced into the exhaust path of the rotary pump 83 by the mass flow meter 86, the pressure of the intermediate chamber R2 kept by the rotary pump 83 can be increased. For example, the pressure initially kept at $10^2$ Pa (pascal) can be increased to $10^3$ Pa.

By constructing the gas conveyor 44 as mentioned, the outside of the outer tube 82 (that is, the inside of the sample chamber R0) can be set at a high pressure, the intermediate chamber R2 can be set at an intermediate pressure, the inside of the inner tube 81 (that is, the inside of the analysis chamber R1) can be set at a low pressure, and these pressures can be kept constant. For example, the sample chamber R0 can be kept at an atmospheric pressure of about $10^5$ Pa, the inside of the intermediate chamber R2 can be kept at an intermediate pressure of about $10^2$ Pa, and the inside of the analysis chamber R1 can be kept in a vacuum state of about $10^{-3}$ Pa. The configuration in which exhaust operation forms an intermediate pressure between a high pressure and a low pressure as mentioned above may be referred to as a differential pumping structure.

The above differential pumping structure reliably achieves a function of conveying the gas generated in the sample chamber R0 via the inner tube 81 to the analysis chamber R1 while a pressure difference is maintained between the sample chamber R0 and the analysis chamber R1 inner pressures of which are different from each other. Here, in the present embodiment, an end of each of the inner tube 81 and the outer tube 82 on a sample chamber R0 side is formed as an orifice (that is, a micro pore), and its facing end on an analysis chamber R1 side is formed as an opening with a normal size not achieving an orifice effect. The diameter of the orifice is, for example, about 100 μm. Forming orifice on the end of each of the inner tube 81 and the outer tube 82 on a sample chamber side, and forming a normal opening on the opposite end of those tubes on an analysis chamber side, as mentioned above, enable to efficiently collect gas generated from the sample S through the orifices and also efficiently convey it to the analysis chamber R1.

According to a gas analyzing apparatus 41 with the above configuration, when a gas is evolved from the sample S heated by means of the heating furnace 47, the evolved gases are carried by means of the gas conveyor 44 to the analysis device 43. Gases thus conveyed are ionized by means of the EI device 74 and the lamp 73 in real time through the both of EI process and PI (soft ionization) process. Then, the both of EI measurement data and PI measurement data are obtained by means of the electrometer 64 at the same time. Later, the processing as shown in FIG. 6 or FIG. 10 is executed by means of arithmetic operation unit 66 of the main control device 53, and thus evolved gases are qualitatively analyzed.

Other Embodiments

While the present invention has been described with reference to the preferred embodiment, it should be apparent that the present invention is not limited to the embodiment and may be embodied in many other specific forms without departing from the spirit or scope of the invention.

For example, in the above descriptions, in order to make the descriptions to be easily understood, mixed gases containing three types of compounds of benzene, toluene and xylene are considered as evolved gases for measurement target. However, it is a matter of course that mixed gases for possible measurement target can be formed by any component gases other than these.

What is claimed is:

1. A gas analyzing method for determining components of a first gas, comprising:
    a first mass analysis step of measuring an intensity of ion obtained from said first gas through an electro impact ionization process;
    a second mass analysis step of measuring an intensity of ion obtained through soft ionization process from a second gas having same concentration of components as those of said first gas;
    a molecular weight determination step of determining molecular weights based on parent ion from data obtained in the second mass analysis step;
    a reference data read-out step of reading out mass spectrums corresponding to molecular components determined in said molecular weight determination step, based on a reference database made by storing mass spectrums of compounds for each compound in case of exciting the compounds through electro impact ionization method; and
    a comparison step of comparing ion intensity data obtained in said first mass analysis step with data read out in said reference data read-out step,
    wherein components of said first gas are determined based on the comparison result in said comparison step.

2. The gas analyzing method according to claim 1, wherein each of said first gas and said second gas is any of,
    gas evolved from one sample at different moments of time,
    gas evolved alternately from one sample at different moments of time within a predetermined time, and
    gas evolved from separate samples obtained by dividing one sample, or gas evolved from separate samples with the same molecular structure.

3. The gas analyzing method according to claim 2,
    wherein molecular weights of a plurality of parent ions are determined through said molecular weight determination step,
    wherein mass spectrums corresponding to each of molecular weights of a plurality of parent ions are read out through said reference data read-out step, and
    wherein said comparison step combines the plurality of mass spectrums to obtain combined mass spectrum, and compares ion intensity data obtained in the first mass analysis step with said combined mass spectrum.

4. The gas analyzing method according to claim 3, wherein intensity ratios among a plurality of parent ions are determined, and mass spectrums read out from the reference database are multiplied by ion intensity ratios.

5. The gas analyzing method according to claim 4, wherein ionization efficiencies of compounds corresponding to said determined molecular components are read out from ionization efficiency database which is made by storing the ionization efficiencies for each molecular weight, and mass spectrums read out from said reference database for each molecular component are multiplied by the ionization efficiencies corresponding to the relevant molecular weights.

6. The gas analyzing method according to claim 2,
wherein molecular weights of a plurality of parent ions are determined through said molecular weight determination step,
wherein mass spectrums corresponding to each of molecular weights of a plurality of parent ions are read out through said reference data read-out step, and
wherein said comparison step compares read-out mass spectrums with ion intensity data obtained in the first mass analysis step on one-by-one basis.

7. The gas analyzing method according to claim 6, wherein a plurality of mass spectrums are compared in the increasing order of molecular weights, and
mass spectrums corresponding to relevant molecules are subtracted after individual comparisons from ion intensity data which are data before the comparisons.

8. The gas analyzing method according to claim 6, wherein intensity ratios among a plurality of parent ions are determined, and mass spectrums read out from the reference database are multiplied by ion intensity ratios.

9. The gas analyzing method according to claim 8, wherein ionization efficiencies of compounds corresponding to said determined molecular components are read out from ionization efficiency database which is made by storing the ionization efficiencies for each molecular weight, and mass spectrums read out from said reference database for each molecular component are multiplied by the ionization efficiencies corresponding to the relevant molecular weights.

10. A gas analyzing apparatus for determining components of a first gas, comprising:
   a first mass analysis means that ionizes said first gas through electro impact ionization process, separates the ion for each m/z, and measures intensity of the ion for each m/z;
   a second mass analysis means that ionizes a second gas having same concentration of components as those of said first gas through soft ionization process, separates the ion for each m/z, and measures intensity of the ion for each m/z;
   a molecular weight determination means that determines molecular weight based on parent ion from data obtained by the second mass analysis means;
   a reference data read-out means that reads out mass spectrums corresponding to molecular weights determined by said molecular weight determination means, based on a reference database made by storing mass spectrums of compounds of single component for each molecular weight of compounds in case of exciting the compounds through electro impact ionization process; and
   a determination means that compares ion intensity data obtained by said first mass analysis means with data read out by said reference data read-out means, and thereby determines components of said first gas.

11. The gas analyzing apparatus according to claim 10,
wherein said molecular weight determination means determines molecular weights of a plurality of parent ions,
wherein said reference data read-out means reads out the mass spectrum corresponding to each of said determined molecular weights of said plurality of parent ions, and
wherein said determination means combines the plurality of mass spectrums to obtain combined mass spectrum, and compares ion intensity data measured by the first mass analysis means with said combined mass spectrum.

12. The gas analyzing apparatus according to claim 11,
wherein said determination means is configured to find intensity ratios among said plurality of parent ions measured by means of the second mass analysis means, and
wherein mass spectrums read out from said reference database are multiplied by ion intensity ratios.

13. The gas analyzing apparatus according to claim 12, further comprising
an ionization efficiency database generated by storing ionization efficiencies of compounds for each molecular component of the compounds,
wherein said determination means reads out ionization efficiencies corresponding to said determined molecular components from said ionization efficiency database, and multiplies mass spectrums for each molecular component read out from said reference database by ionization efficiencies corresponding to the relevant molecular component.

14. The gas analyzing apparatus according to claim 10,
wherein said molecular weight determination means determines molecular weights of a plurality of parent ions,
wherein said reference data read-out means reads out the mass spectrum corresponding to each of said determined molecular weights of said plurality of parent ions, and
wherein said determination means compares read out mass spectrums with ion intensity data measured by said first mass analysis means on one-by-one basis.

15. The gas analyzing apparatus according to claim 14,
wherein said determination means compares read out mass spectrums in the increasing order of molecular weights, and
after individual comparison has been done, subtracts mass spectrums corresponding to the relevant molecular weights from ion intensity data which are data before the comparisons.

16. The gas analyzing apparatus according to claim 15,
wherein said determination means is configured to find intensity ratios among said plurality of parent ions measured by means of the second mass analysis means, and
wherein mass spectrums read out from said reference database are multiplied by ion intensity ratios.

17. The gas analyzing apparatus according to claim 16, further comprising
an ionization efficiency database generated by storing ionization efficiencies of compounds for each molecular component of the compounds,
wherein said determination means reads out ionization efficiencies corresponding to said determined molecular components from said ionization efficiency database, and multiplies mass spectrums for each molecular component read out from said reference database by ionization efficiencies corresponding to the relevant molecular component.

* * * * *